United States Patent
Li et al.

(10) Patent No.: US 11,945,853 B2
(45) Date of Patent: Apr. 2, 2024

(54) GENETICALLY MODIFIED PROBIOTICS FOR ORAL DELIVERY OF RENIN-ANGIOTENSIN RELATED THERAPEUTIC PROTEINS AND PEPTIDES

(71) Applicant: UNIVERSITY OF FLORIDA RESEARCH FOUNDATION, INCORPORATED, Gainesville, FL (US)

(72) Inventors: Qiuhong Li, Gainesville, FL (US); Mohan Raizada, Alachua, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 106 days.

(21) Appl. No.: 17/839,815

(22) Filed: Jun. 14, 2022

(65) Prior Publication Data
US 2023/0036131 A1    Feb. 2, 2023

Related U.S. Application Data

(62) Division of application No. 16/333,044, filed as application No. PCT/US2017/051423 on Sep. 13, 2017, now Pat. No. 11,377,479.

(60) Provisional application No. 62/394,137, filed on Sep. 13, 2016.

(51) Int. Cl.
| | |
|---|---|
| C07K 14/575 | (2006.01) |
| A61K 35/00 | (2006.01) |
| A61K 35/74 | (2015.01) |
| A61K 35/741 | (2015.01) |
| A61K 35/747 | (2015.01) |
| A61K 45/06 | (2006.01) |
| A61K 48/00 | (2006.01) |
| A61P 3/00 | (2006.01) |
| A61P 3/10 | (2006.01) |
| A61P 9/12 | (2006.01) |
| A61P 27/02 | (2006.01) |
| A61P 29/00 | (2006.01) |
| C07K 7/14 | (2006.01) |
| C07K 14/195 | (2006.01) |
| C07K 14/28 | (2006.01) |
| C07K 14/47 | (2006.01) |
| C07K 19/00 | (2006.01) |
| C12N 1/00 | (2006.01) |
| C12N 9/48 | (2006.01) |

(52) U.S. Cl.
CPC ............ *C07K 14/575* (2013.01); *A61K 35/74* (2013.01); *A61K 35/741* (2013.01); *A61K 35/747* (2013.01); *A61K 45/06* (2013.01); *A61P 3/00* (2018.01); *A61P 3/10* (2018.01); *A61P 9/12* (2018.01); *A61P 27/02* (2018.01); *A61P 29/00* (2018.01); *C07K 7/14* (2013.01); *C07K 14/195* (2013.01); *C07K 14/28* (2013.01); *C07K 14/47* (2013.01); *C07K 19/00* (2013.01); *C12N 1/00* (2013.01); *C12N 9/485* (2013.01); *A61K 2035/115* (2013.01); *A61K 48/00* (2013.01); *C07K 2319/02* (2013.01); *C07K 2319/50* (2013.01); *C07K 2319/60* (2013.01)

(58) Field of Classification Search
None
See application file for complete search history.

(56) References Cited

U.S. PATENT DOCUMENTS 10,314,893 B2 *  6/2019  Daniell ................. A61K 9/19

FOREIGN PATENT DOCUMENTS

WO    2018053049 A1    3/2018

OTHER PUBLICATIONS

Cole-Jeffrey, Colleen T. et al., "ACE2 and Microbiota: Emerging Targets for Cardiopulmonary Disease Therapy", J. Cardiovasc Pharmacol, Dec. 2015, vol. 66, No. 6, pp. 540-550.
Dominici, Fernando P. et al., "Modulation of the action of insulin by angiotensin-(1-7)," Clinical Science, 2014, vol. 126, pp. 613-630.
Heringer-Walther, Silvia et al., "Angiotensin-(1-7) stimulates hematopoietic progenitor cells in vitro and in vivo", Haematologica, 2009, vol. 94, No. 6, pp. 857-860.
Jatajapu, Yagna P.R. et al., "Activation of the ACE2/Angiotensin-(1-7)/Mas Receptor Axis Enhances the Reparative Function of Dysfunctional Diabetic Endothelial Progenitors", Diabetes, Apr. 2013, vol. 62, pp. 1258-1269.
Menon, Jyotsana et al., "Antiotensin-(1-7) Inhibits Growth of Human Lung Adenocarcinoma Xenografts in Nude Mice through a Reduction in Cyclooxygenase-2", Cancer Res, Mar. 15, 2007, vol. 67, No. 6, pp. 2809-2819.

(Continued)

*Primary Examiner* — Suzanne M Noakes
*Assistant Examiner* — Jae W Lee
(74) *Attorney, Agent, or Firm* — Timothy H. Van Dyke; WOLTER, VAN DYKE, DAVIS, PLLC

(57) ABSTRACT

Provided herein are polynucleic acids and expression vectors for the expression and secretion of angiotensin peptide fragments (e.g., angiotensin-(1-7)) in probiotic bacteria. Provided herein are also probiotic compositions that enable efficient, cost-effective and patient friendly oral therapeutics for treating diverse pathological conditions that involve the renin-angiotensin system (RAS), e.g., pulmonary hypertension, diabetes, diabetic complications, cardiovascular diseases, and ocular inflammatory and neurodegenerative diseases.

21 Claims, 21 Drawing Sheets
Specification includes a Sequence Listing.

(56) References Cited

OTHER PUBLICATIONS

Passos-Silva, Danielle G. et al., "Antiotensin-(1-7): beyond the cardio-renal actions", Clinical Science, 2013, vol. 124, pp. 443-456.
Pereira, Regina Marie et al., "The renin-angiotensin system in a rat model of hepatic fibrosis: Evidence for a protective role of Angiotensin-(1-7)", Journal of Hepatology, 2007, vol. 46, pp. 674-681.
Qi, YanFei et al., "Diminazene Aceturate Enhances Angiotensin-Converting Enzyme 2 Activity and Attenuates Ischemia-Induced Cardiac Pathophysiology", Hypertension, Oct. 2013, 746-752.
Qiu, Yiguo et al., "Angiotensin-Converting Enzyme 2 (ACE2) Activator Diminazene Aceturate Ameliorates Endotoxin-Induced Uveitis in Mice", Invest Ophthalmol Vis Sci., 2014, vol. 55, pp. 3809-3818.
Santos, Robson A.S. et al., "Angiotensin-(1-7) is an endogenous ligand for the G protein-coupled receptor Mas", PNAS, Jul. 8, 2003, vol. 100, No. 14, pp. 8258-8263.
Santos, Robson Augusto, "Angeiotensin-(1-7)", Hypertension, 2014, vol. 63, pp. 1138-1147.
Santos, Robson, A.S. et al., "Expression of a angiotensin-(1-7)-producing fusion protein produces cardioprotective effects in rats", Physiol Genomics, 2004, vol. 17, pp. 292-299.
Santos, Robson A.S. et al., "Angiotensin-(1-7): an update", Regulatory Peptides, 2000, vol. 91, pp. 45-62.
Santos, Sergio Henrique Sousa et al., "Angiotensin 1-7: A peptide for preventing and treating metabolic syndrome", Peptides, 2014, vol. 59, pp. 34-41.
Schiavone, Marc T. et al., "Release of vasopressin from the rat hypothalamuspophysial system by angiotensin-(1-7) heptapeptide", Proc. Natl. Acad. Sci. USA, Jun. 1988, vol. 85, pp. 4095-4098.
Shenoy, Vinayak et al., "Diminazene Attenuates Pulmonary Hypertension and Improves Angiogenic Progenitor Cell Functions in Experimental Models", Am J. Respir. Crit. Care Med., Mar. 15, 2013, vol. 187, iss. 6, pp. 648-657.
Shenoy, Vinayak et al., "The Angiotensin-Converting Enzyme 2/Angiogenesis-(1-7)/Mas Axis Confers Cardiopulmonary, Protection against Lung Fibrosis and Pulmonary Hypertension", Am. J. Respir. Crit. Care Med., 2010, vol. 182, pp. 1065-1072.
Shenoy, Vinayak et al., "Oral Delivery of Angiotensin-Converting Enzyme 2 and Angiotensin-(1-7) Bioencapsulated in Plant Cells Attenuates Pulmonary Hypertension", Hypertension, Dec. 2014, vol. 64, No. 6, pp. 1248-1259.
Shil, Pollob K. et al., "Oral Delivery of ACE2/Ang-(1-7) Bioencapsulated in Plant Cells Protects against Experimental Uveitis and Autoimmune Uveoretinitis", Molecular Therapy, Dec. 2014, vol. 22, No. 12, pp. 2069-2082.
Silva, AC Simoes E. et al., "ACE2, angiotensin-(1-7) and Mas receptor axis in inflammation and fibrosis", British Journal of Pharmacology, 2013, vol. 169, pp. 477-492.
Loot, Annemarieke E. et al., "Angiotensin-(1-7) Attenuates the Development of Heart Failure After Myocardial Infarction in Rats", Circulation, Apr. 2, 2002, vol. 105, pp. 1548-1550.
Verma, Amrisha et al., "ACE2 and Ang-(1-7) Confer Protective Against Development of Diabetic Retinopathy" Molecular Therapy, Jan. 2012, vol. 20, No. 1, pp. 28-36.
Yang, Guilian et al., "Effective treatment of hypertension by recombinant Lactobacillus plantarum expressing angiotensin converting enzyme inhibitory peptide", Microb Cell Fact, 2015, vol. 14, No. 22, 9 pages.
Campagnole-Santos, Maria J. et al., "Cardiovascular effects of angiotensin-(1-7) injected into the dorsal medulla of rats", The American Physiological Society, 1989, pp. H324-H329.
Santos, R.A.S. et al., "Angiotensin-(1-7): Blood, Heart, and Blood Vessels", Curr. Med. Chem.-Cardiovascular & Hematoligical Agents, 2005, vol. 3, pp. 383-391.

* cited by examiner

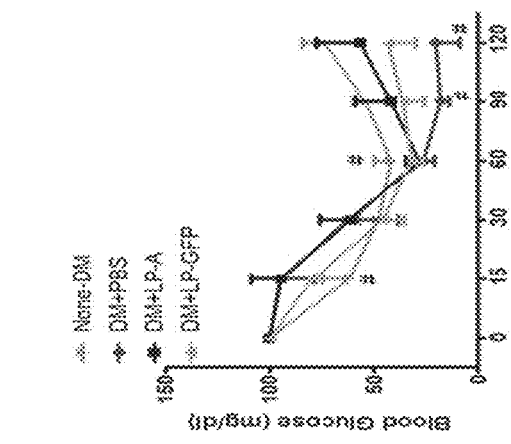
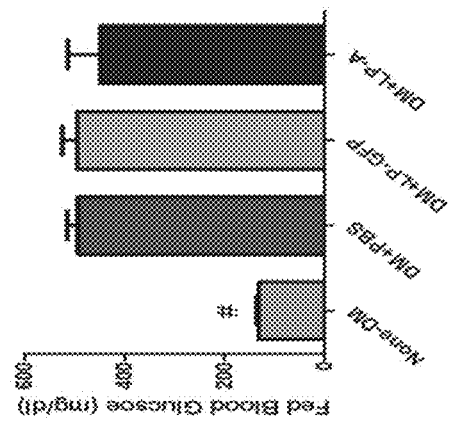
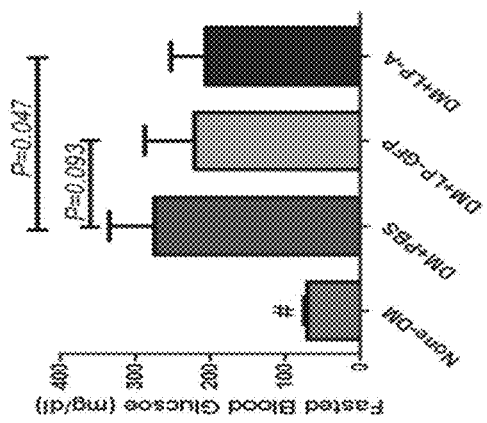
FIG. 10A, FIG. 10B, FIG. 10C, FIG. 10D, FIG. 10E GENETICALLY MODIFIED PROBIOTICS FOR ORAL DELIVERY OF RENIN-ANGIOTENSIN RELATED THERAPEUTIC PROTEINS AND PEPTIDES

GOVERNMENT SUPPORT

This invention was made with government support under grant numbers EY024564 and HL102033 awarded by the National Institutes of Health. The government has certain rights in the invention.

BACKGROUND

The protective effects of angiotensin-(1-7)[Ang-(1-7)] in diverse pathological conditions have been well established. However, Ang-(1-7) gets rapidly degraded in circulation and various tissues, including the stomach, making it challenging to develop an oral pharmaceutical composition of Ang-(1-7) that delivers the peptide to target tissue and secure its bioavailability. Expressing Ang-(1-7) from an expression vector is also challenging given that it is only seven amino acids long.

SEQUENCE LISTING

The instant application contains a Sequence Listing which has been submitted in ASCII format via EFS-Web and is hereby incorporated by reference in its entirety. Said ASCII copy, created on Mar. 22, 2018 is named sequencelisting.txt and is 18 KB in size.

SUMMARY

The present application provides polynucleic acids, expression vectors and probiotic compositions that can effectively deliver small peptides and proteins to target tissues via oral administration for treatment of diseases and conditions involving the renin-angiotensin system (RAS).

In some embodiments, probiotic compositions provided herein comprise probiotic bacteria that are genetically engineered to express and secrete Ang-(1-7) and/or ACE2, and contain expression vectors encoding a fusion protein comprising Ang-(1-7) or ACE2 and a carrier protein, e.g., cholera toxin B (CTB), that allows easy transportation of the fusion protein through transmucosal membranes into the circulation and target tissue. The present disclosure partly relates to, as one embodiment, the design of a furin cleavage site between the Ang-(1-7) or ACE2 and CTB so that the fusion protein can be cleaved. The present disclosure relates, at least in part, to the surprising discovery that even though furin is ubiquitously present in many tissues and cell types, Ang-(1-7) expressed in probiotic bacterium that is administered orally is delivered to target tissues and in sufficient amounts so as to cause therapeutic benefit. The inventors also found, surprisingly, that probiotics themselves (that do not express Ang-(1-7) or ACE2) provide a therapeutic benefit (demonstrated in the examples provided herein). Accordingly, in some embodiments, a composition comprising probiotic bacteria that are not genetically engineered to express any peptides or proteins are administered (e.g., alone or in addition to probiotic bacteria that express one or more peptides).

The probiotic-based delivery of Ang-(1-7) and/or ACE2 as disclosed herein offers many advantages. (1) probiotics are safe to consume, and offer many beneficial health effects on their own. (2) oral delivery is a preferred delivery route for drugs that have to be administered regularly, particularly for patients with chronic diseases such as diabetes. Oral delivery of therapeutics is patient-friendly and also eliminates the cost for trained professionals required for other routes of administration. (3) food-grade probiotics expressing Ang-(1-7) and/or ACE2 can be easily scaled-up using current technology, which will significantly reduce the cost. Since such probiotics are considered nutritional supplements, they do not need to be FDA-approved. (4) CTB fusion facilitates efficient transmucosal transport of Ang-(1-7) and/or ACE2 into the circulation and target tissue and also prevents its degradation, thus enhancing the bioavailability of Ang-(1-7) and/or ACE2. (5) there is minimal risk of contamination with human pathogens or toxins that are usually encountered in bacterial, yeast or mammalian cell culture systems currently used to produce therapeutic proteins. (6) there is minimal or practically no risk of immune responses to orally delivered therapeutic proteins, and in fact oral protein delivery has been used as a strategy to induce immune tolerance [32-34]. Probiotics are known to promote gastrointestinal health by modulating the immune system, among many other protective actions [35-37].

Accordingly, in certain aspects, provided herein is a polynucleic acid for expressing a peptide or protein (e.g., Ang-(1-7) or ACE2) in a bacterium (e.g., a probiotic bacterium) that can be used for oral delivery by feeding. In some embodiments, a polynucleic acid comprises a promoter, a nucleic acid encoding a secretion signal peptide, a nucleic acid encoding a carrier protein, a nucleic acid encoding either Ang-(1-7) or ACE2, and a nucleic acid encoding a cleavage site. In some embodiments, a cleavage site lies in between nucleic acids encoding the carrier protein and Ang-(1-7) or ACE2. In some embodiments, the nucleic acids encoding the secretion signal peptide, carrier protein, Ang-(1-7) or ACE2, and a cleavage site encode a fusion protein and are operably linked to the promoter.

In some embodiments of any one of the polynucleic acids encoding ACE2 provided herein, no cleavage site exists between the carrier protein and ACE2.

In some embodiments, any one of the polynucleic acids provided herein further comprises a nucleic acid encoding a hinge. A hinge may lie 3' to a nucleic acid encoding a carrier protein. A hinge may lie 5' to a nucleic acid encoding a cleavage site or ACE2 or Ang-(1-7).

In some embodiments, any one of the polynucleic acids provided herein further comprises a terminator. A terminator may lie 3' to the nucleic acid encoding Ang-(1-7) or ACE2.

In some embodiments of any one of the polynucleic acids provided herein, a promoter is a lactose dehydrogenase (ldh) promoter from *Lactococcus lactis*. In some embodiments, the sequence of a ldh promoter is at least 95% identical to SEQ ID NO: 1. In some embodiments, the sequence of a ldh promoter is SEQ ID NO: 1.

In some embodiments, a secretion signal peptide is from the usp45 gene of *Lactococcus lactis*. In some embodiments, the sequence of a nucleic acid encoding a secretion signal peptide from usp45 gene of *Lactococcus lactis* is at least 95% identical to SEQ ID NO: 2. In some embodiments, the sequence of a nucleic acid encoding a secretion signal peptide from usp45 gene of *Lactococcus lacti* is SEQ ID NO: 2.

In some embodiments, a nucleic acid encoding a secretion signal peptide lies adjacent and 5' to the nucleic acid encoding the carrier protein.

In some embodiments of any one of the polynucleic acids disclosed herein, a carrier protein is cholera toxin B (CTB). In some embodiments, the sequence of a nucleic acid encoding CTB is at least 95% identical to SEQ ID NO: 3. In some embodiments, the sequence of a nucleic acid encoding CTB is SEQ ID NO: 3.

In some embodiments, a carrier protein is a cell-penetrating peptide (CPP) derived from Pancreatic And Duodenal Homeobox 1 (PDX-1). In some embodiments, the sequence of the nucleic acid encoding a CPP derived from PDX-1 is at least 95% identical to SEQ ID NO: 18. In some embodiments, the sequence of the nucleic acid encoding CTB is SEQ ID NO: 18.

In some embodiments of any one of the polynucleic acids encoding Ang-(1-7) disclosed herein, the sequence of the nucleic acid encoding Ang-(1-7) is SEQ ID NO: 4.

In some embodiments of any one of the polynucleic acids encoding ACE2 disclosed herein, the sequence of a nucleic acid encoding ACE2 is at least 95% identical to SEQ ID NO: 7.

In some embodiments, the sequence of a nucleic acid encoding ACE2 is SEQ ID NO: 7.

In some embodiments, a cleavage site is a furin cleavage site. In some embodiments, the sequence of a nucleic acid encoding a hinge and a furin cleavage site is SEQ ID NO: 5.

In some embodiments, a terminator sequence is SEQ ID NO: 6.

In some embodiments, any of the polynucleic acids provided herein further comprise a nucleic acid encoding a detectable molecule. A detectable molecule may be encoded such that is fused to Ang-(1-7) or ACE2. In some embodiments, a detectable molecule is a fluorescent protein, bioluminescent protein, or an enzyme that provides formation of a colored product that can be visualized.

In some embodiments, any one of the polynucleic acids encoding Ang-(1-7) provided herein further comprise nucleic acids that encode a second cleavage site, a second carrier protein, a third cleavage site and either ACE2 or Ang-(1-7). In some embodiments, nucleic acids encoding the secretion signal peptide, the carrier protein, the cleavage site, Ang-(1-7), the second cleavage site, the second carrier protein, the third cleavage site and ACE2 encode a fusion protein and are operably linked to the promoter. Such polynucleic acids encode a fusion protein comprising both Ang-(1-7) and ACE2.

Expression vectors are useful for transforming a bacterium to either express and secrete a peptide or protein ectopically, or transform a bacteria so that the expression vector is integrated into the genome of the bacteria. Accordingly, in some aspects, provided herein are expression vectors comprising any one of the polynucleic acids provided herein. In some embodiments, expression vectors disclosed herein comprise polynucleic acids that encode a fusion protein comprising a peptide or protein, which upon secretion is cleaved to provide the peptide or protein and a carrier protein to which the peptide or protein was fused. In some embodiments, an expression vector comprises one or more antibiotic resistance genes. In some embodiments, an antibiotic resistance gene is resistant to nisin. In some embodiments, an expression vector is an integration vector that can be integrated into the genome of a bacterium. In some embodiments, an integration vector lacks an origin of replication and antibiotic resistant genes.

Bacterium that is probiotic or commensal provide a health benefit when administered orally into the gut of a subject. Accordingly, in some aspects, provided herein is a genetically engineered bacterium comprising any one of the expression vectors provided herein. In some embodiments, a bacterium that is genetically modified by transformation of any one of the expression vectors disclosed herein is commensal or probiotic. In some embodiments, a bacterium is a *Lactobacillus*. In some embodiments, a *Lactobacillus* is a probiotic species of *Lactobacillus* genus. In some embodiments, a *Lactobacillus* is *L. paracasei, L. plantarum,* or *L. gasseri*. In some embodiments, a *Lactobacillus* is *L. casei, L. helveticus, L. reuteri,* or *L. rhamnosus*. In some embodiments, a combination of two or more (e.g., 3, 4, 5, or more) *Lactobacillus* probiotic species is used. In some embodiments, other probiotic bacteria can be used, including, but not limited to: *Bifidobacterium* species (e.g., *B. bifidum, B. longum, B. infantis*), *Bacillus* species (*B. coagulans*), and/or *Streptoccocus* species (e.g, *S. salivarius* K12, S. *Salivarius* M18).

A probiotic substance is one that stimulates the growth of microorganisms, especially those with beneficial properties (such as those of the intestinal flora). Probiotic compositions comprising probiotic or commensal bacterium provide a health benefit when fed to a subject orally (e.g., boosting immune system, preventing urinary tract infections, improving digesting function, healing inflammatory bowel conditions, aid in the management of eczema or fight food-borne illnesses). Accordingly, in some aspects, provided herein are probiotic compositions comprising a plurality of any one of the genetically engineered bacterium provided herein. In some embodiments, a probiotic composition comprises genetically engineered bacteria that are live and concentrated. In some embodiments, a probiotic composition is frozen, in the form or lyophilized powder, or in the form of a tablet formed from lyophilized powder.

The renin-angiotensin system (RAS) affects many diseases and conditions. Thus, modulating the RAS can be an effective strategy to treat RAS-related diseases. Moreover, oral delivery of therapeutics, especially those that need to be administered to a subject chronically, benefit from oral administration. Accordingly, in some aspects, provided herein are methods of treating a disease or condition involving RAS comprising administering orally to a subject in need thereof a therapeutically effective dose of any one of the probiotic compositions provided herein. In some embodiments, a method of treating a disease or condition involving RAS comprises administering orally to a subject in need thereof a therapeutically effective dose of a probiotic composition comprising genetically modified bacterium expressing Ang-(1-7) and genetically modified bacterium expressing ACE2. In some embodiments, genetically modified bacterium expressing Ang-(1-7) and genetically modified bacterium expressing ACE2 are comprised in separate compositions.

In some embodiments, a disease or condition involving the RAS is an age-related neurodegenerative disease, nephropathy, obesity, a metabolic disease, a cardiovascular disease or an ocular inflammatory disease or condition. In some embodiments, a disease or condition involving the RAS is pulmonary hypertension, diabetes, a diabetes-associated complication or an ocular inflammatory disease or condition.

In some embodiments, a metabolic disease is diabetes or insulin resistance.

In some embodiments, an age-related neurodegenerative disease is age-related macular degeneration, Alzheimer's disease or Parkinson's disease.

In some embodiments, a cardiovascular disease is hypertension, heart failure, a coronary artery disease or atherosclerosis.

In some embodiments, a diabetes-associated complication is diabetic nephropathy or diabetic retinopathy.

In some embodiments, an ocular inflammatory disease or condition is scleritis or uveitis. Uveitis can be an anterior uveitis, intermediate uveitis or posterior uveitis. A posterior uveitis can be choroiditis, retinal vasculitis, retinitis, neuroretinitis, retinochoroiditis or chorioretinitis.

In some embodiments, a method of treating a disease or condition involving the renin-angiotensin system (RAS) further comprises administering to the subject an activator of ACE2.

In some embodiments, methods and compositions described in this application can be administered to a subject (e.g., a human subject) to treat and/or prevent MCT-induced gut dysbiosis, treat and/or prevent diabetes and its associated renal and retinal complications, improve glucose tolerance and insulin sensitivity, prevent diabetes-induced destruction of insulin producing cells, increase insulin levels in diabetic subjects, alleviate kidney damage in diabetic subjects, prevent diabetes-induced retinal capillary loss, reduce diabetes-induced retinal ganglion cell loss, reduce gliosis and expression of inflammatory cytokines in diabetic retina, and/or prevent autoimmune uveitis.

These and other aspects are described in more detail in the description and illustrated by the non-limiting examples and drawings.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the description and data illustrated in the drawings in no way limit the scope of the disclosure.

FIG. 1 provides a diagram of one embodiment of the disclosed expression vector for use in *lactobacillus*. The gene of interest, for example the Ang-(1-7) shown in the diagram, is under the control of ldh promoter, and expressed as a secreted fusion protein to a mutant CTB which lacks immune modulating activity but maintains the GM1 binding essential for transepithelial transport into circulation and tissue uptake of the expressed protein. The CTB is separated by a furin cleavage site to release Ang-(1-7) once it is expressed. The codon usage for all coding sequences is optimized for highest expression in *lactobacillus*.

FIG. 2 shows an ELISA measurement of tissue levels of secreted GFP in mice fed with *Lactobacillus paracasei* engineered to express CTB-GFP. GFP is efficiently expressed and taken up by different tissues (N=4).

FIG. 4A. Measurement of right ventricular (RV) systolic pressure (RVSP) in normal controls and MCT-challenged rats that were either untreated or orally fed with *L. paracasei* (LP), LP-GFP (LP-G), or LP-Ang-(1-7) (LP-A). Data shown are mean±SEM. *p<0.0001 vs control rats, **p<0.001 vs control rats, and #p<0.05 vs MCT rats. FIG. 4B. Measurement of right ventricular (RV) hypertrophy, measured as the ratio of RV to left ventricle (LV) plus interventricular septum (S) weights [RV/(LV+S)] in normal controls and MCT-challenged rats that were either untreated or orally fed with LP, LP-G, or LP-A. Data shown are mean±SEM. *p<0.0001 vs control rats, **p<0.01 vs control rats, and #p<0.05 vs MCT rats. FIG. 4C. Measurement of +dP/dt in normal controls and MCT-challenged rats that were either untreated or orally fed with LP, LP-G, or LP-A. Data shown are mean±SEM. *p<0.05 vs control rats and #p<0.05 vs MCT rats. FIG. 4D. Measurement of −dP/dt in normal controls and MCT-challenged rats that were either untreated or orally fed with LP, LP-G, or LP-A. Data shown are mean±SEM. *p<0.0001 vs control rats, p<0.001 vs control rats, and *p<0.05 vs control rats. N=6 to 8 animals/group for FIGS. 4A-4D.

FIGS. 10A-10E show that oral delivery of Ang-(1-7)-*Lactobacillus paracasei* (LP-A) improved hyperglycemia and glucose tolerance in diabetic mice. (A-B) Blood glucose concentrations in fed- (FIG. 10A) and fasted-state (FIG. 10B) in mice. GTT in 16-hour-fasted mice (FIG. 10C) and area under the curve (AUC) calculated and analyzed for this GTT (FIG. 15D). Insulin tolerance test (ITT) of 6-hour-fasted mice (FIG. 10E). Values are mean±SD; #, compared with other three groups P<0.05; *, compared with DM+PBS group P<0.05, n=6-8/group.

(FIG. 11A) Histological assessment with Periodic Acid Schiff (PAS) staining and Masson trichrome staining; (FIG. 11B) Representative images of the TUNEL assay showing apoptotic cells and quantification of TUNEL-positive cells, #P<0.001, compared with DM+PBS and DM+GFP; n=6.each group. NDM: none—diabetic.

FIGS. 12 A and B: Representative images of trypsin-digested retinal vascular preparations from nondiabetic eNOS−/−, untreated, and LP-A treated diabetic eNOS−/− mouse retinas (FIG. 12A) and untreated and LP-A treated Akita mouse retinas (FIG. 12B), and quantitative measurements of acellular capillaries of eNOS (FIG. 12C) and Akita (FIG. 12D) mice. Arrows indicate the acellular capillaries. NDM, non-diabetes; DM, diabetes. N=6. # (p<0.01): versus non-diabetic control; *(p<0.05 (versus untreated DM groups). Treatments with LP-A significantly reduced acellular capillaries in both eNOS and Akita mice. LP alone also showed small but significant reduction of capillary loss in diabetic eNOS mice.

DETAILED DESCRIPTION

Figure 3:
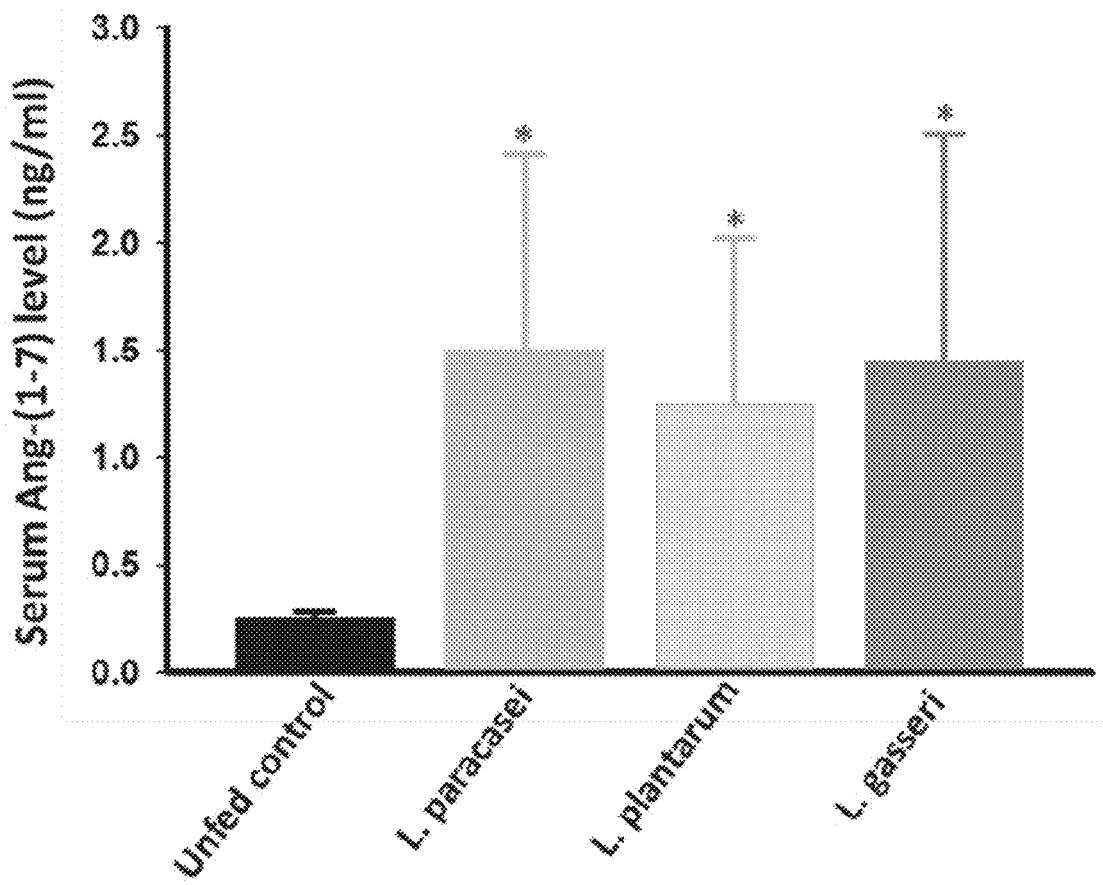
FIG. 3 shows serum levels of Ang-(1-7) in mice fed with different strains of *lactobacillus* that are genetically engineered to express Ang-(1-7). Ang-(1-7) is efficiently expressed and secreted into circulation using three probiotic strains. N=4. *p<0.001 (versus unfed control).
Figure 4A:
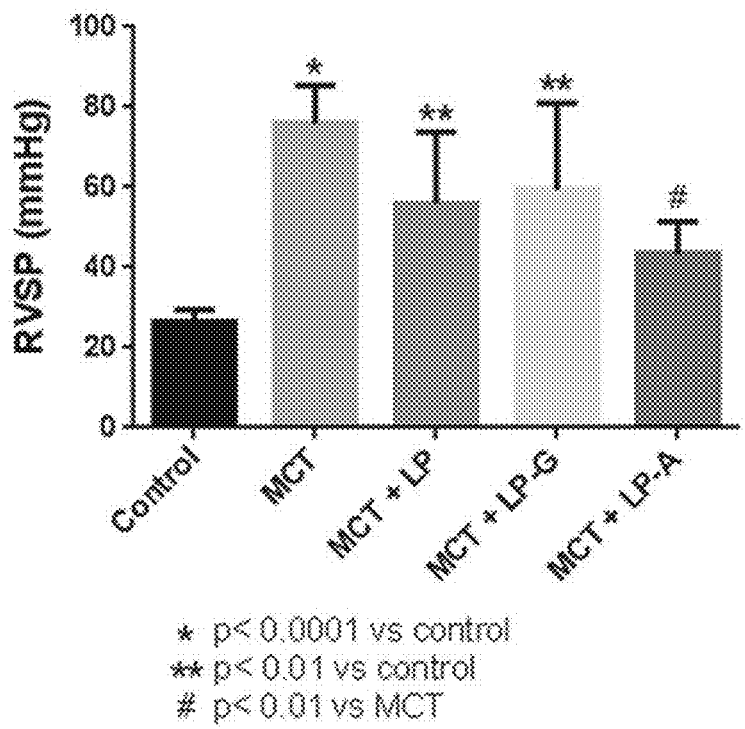
FIGS. 4A-4D show that oral administration of *Lactobacillus paracasei* engineered to express LP-angiotensin-(1-7) [Ang-(1-7)] (LP-A) prevents monocrotaline (MCT)-induced pulmonary hypertension.
Figure 4B:
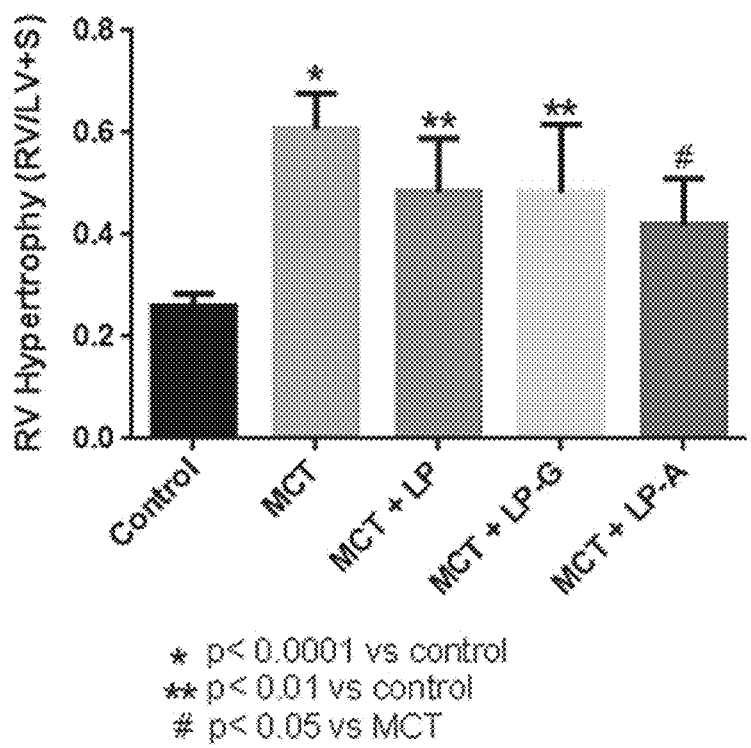
Figure 4C:
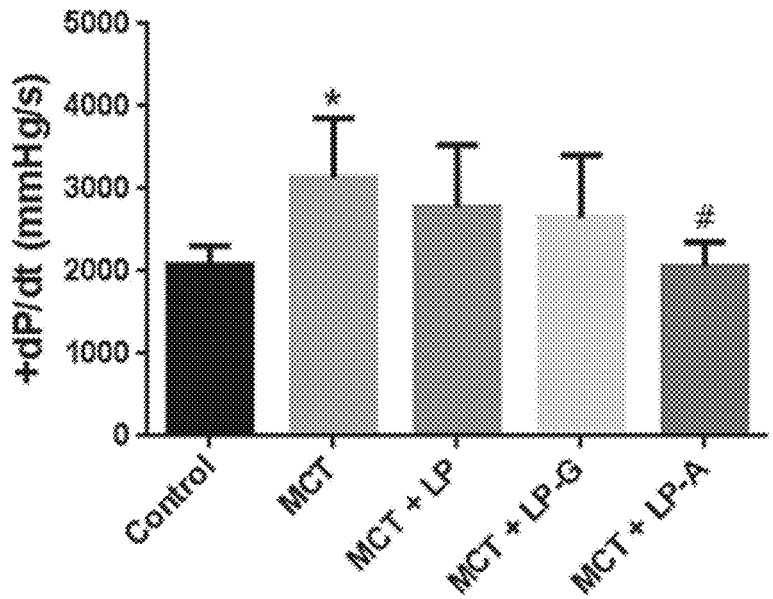
Figure 4D:
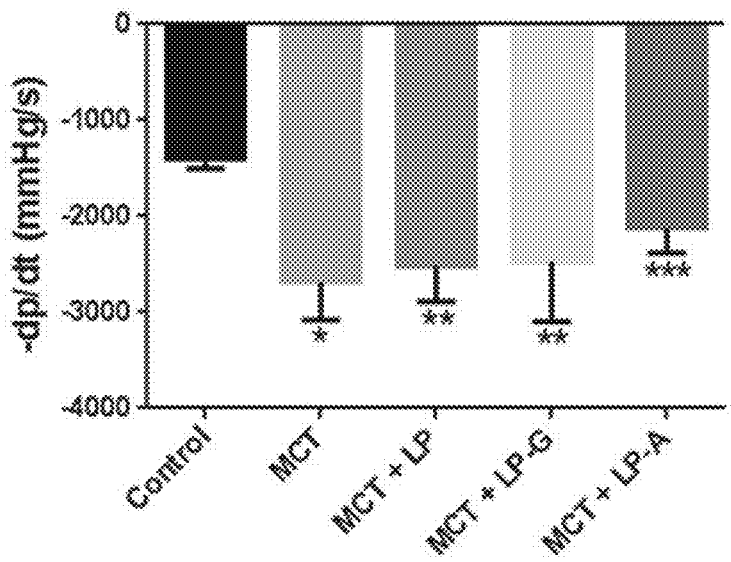

The renin angiotensin system (RAS) plays a vital role in regulating the normal physiological functions of the cardiovascular and renal systems. In addition to systemic RAS, all components of RAS exist in all organs. Tissue RAS has an important role in mediating diverse physiological functions. Dysfunction of RAS, resulting in elevated level of Angiotensin II (Ang II), contributes to pathogenesis of a variety of cardiovascular, metabolic and degenerative diseases by increasing inflammation, oxidative stress, endothelial dysfunction and fibrosis. Angiotensin (1-7) (Ang-(1-7)) is a peptide hormone in the RAS, mainly formed from degradation of Angiotensin II (Ang II) by angiotensin converting enzyme 2 (ACE2) [1]. Ang-(1-7) counteracts the deleterious effects of Ang II by binding to Mas receptor [2-4] and activating downstream protective pathways that induce vasodilation, positive regulation of insulin secretion, antiproliferative, anti-oxidative, and anti-inflammatory activities [5-9]. In previous work, the inventors firmly established the protective effects of Ang-(1-7) in pulmonary hypertension [10-13] and ocular inflammatory and degenerative diseases [14-16].

Overwhelming evidence has confirmed the beneficial effects of Ang-(1-7) in cardiovascular, renal pathology, and metabolism. In addition to protective action in glucose and lipid metabolism, improving insulin sensitivity and reducing diabetic complications, Ang-(1-7) has many other therapeutic actions, including cardiovascular effects [17-20], antitumor effects [21], stimulation of hematopoietic progenitor cells [22, 23], wound healing, antifibrotic effects [18] and attenuation of neointima formation [24]. As a result, there is a tremendous interest for its therapeutic application [25-27]. Several phase I/II clinical trials have already begun with the use of Ang-(1-7) in chemotherapy-induced cytopenias in cancer patients [28] and in patients with advanced cancer [29].

Despite and possibly because of the ubiquitous nature of the RAS, this 7-amino acid peptide, Ang-(1-7) is difficult to develop as a therapeutic. This is because Ang-(1-7) gets rapidly degraded by several peptidases present in the circulation and many tissues [30, 31]. An oral composition of Ang-(1-7) is particularly challenging to develop because there is substantial degradation of Ang-(1-7) in the stomach. Furthermore, expressing Ang-(1-7) alone is difficult because of its small size.

As a solution to these problems, the inventors have developed a novel expression and delivery system based on utilization of genetically modified probiotic bacteria to express and secrete Ang-(1-7) from the gut of a subject into circulation and target tissues following oral administration. This novel approach provides a therapeutically efficient, cost-effective, and patient friendly delivery of Ang-(1-7) for treating a variety of diseases and conditions that involve RAS, e.g., pulmonary hypertension, diabetes, diabetic complications and ocular inflammatory diseases. As described herein, compared to strategies based on expression systems for mammalian cells, treating disease by administering an oral formulation comprised of genetically modified probiotic bacteria that express and secrete Ang-(1-7) can be advantageous since such bacteria can prove to be a persistent source of therapeutic protein and also provide added benefits that probiotics manifest in general. The inventors found that probiotics that do not express and secrete Ang-(1-7) also provided a therapeutic effect, underscoring the unexpected advantage of using probiotic bacteria as a vehicle for Ang-(1-7).

Accordingly, provided herein are polynucleic acids, vectors, genetically modified bacteria, pharmaceutical compositions for oral administration and methods for the treatment of a disease or condition involving the RAS.

Polynucleic Acids

In some embodiments, a polynucleic acid comprises a promoter, a nucleic acid encoding a secretion signal peptide, a nucleic acid encoding a carrier protein, a nucleic acid encoding Ang-(1-7), and a nucleic acid encoding a cleavage site that lies in between the nucleic acids encoding the carrier protein and Ang-(1-7). The polynucleic acid thus encodes a fusion protein comprising a secretion signal peptide, a carrier protein, a cleavage site and Ang-(1-7). The nucleic acid encoding the fusion protein is operably linked to the promoter.

In some embodiments, similar polynucleic acids are provided that expresses ACE2 instead of Ang-(1-7). Some embodiments of a polynucleic acid encoding ACE2 exclude a cleavage site.

In some embodiments, similar polynucleic acids are provided that express other angiotensin peptides, for example, Ang-(1-8), Ang-(2-8), Ang-(1-9), Ang-(2-9), or other related peptides, including those described in this application.

A polynucleic acid is a biopolymer composed of multiple (e.g., more than 5, 10 or 15) nucleotide monomers covalently bonded in a chain. Polynucleic acids can comprise either DNA or RNA molecules or a combination thereof.

Promoter

In some embodiments, a promoter is a lactate dehydrogenase promoter (ldh) promoter. In some embodiments, a ldh promoter is from a species of *Lactococcus*, e.g., *Lactococcus lactis*. In some embodiments, a ldh promoter has the sequence of SEQ ID NO: 1, or is a fragment or variant of a promoter having a sequence of SEQ ID NO: 1. In some embodiments a promoter has at least 80%, 85%, 90%, 95%, 96%, 97%, 98%, 99% or 100% sequence identity to SEQ ID NO: 1. In some embodiments, a promoter is a fragment of the promoter defined by SEQ ID NO: 1, and may be 1-200 (e.g., 1, 5, 10, 20, 50, 100 or 200) nucleotides shorter than the promoter defined by SEQ ID NO: 1. In some embodiments, a promoter has at least 80%, 85%, 90%, 95%, 96%, 97%, 98%, 99%, 100%, or more of the activity (e.g., promotion of transcription of a gene) of that of a promoter that has a sequence of SEQ ID NO:1.

Nucleotide Sequence of a Non-Limiting Example of a Ldh Promoter from *Lactococcus lactis*:

```
                                         (SEQ ID NO: 1)
caagtctcctttttttattagtgataattttaacaaagaaaattataccat gttgaagagcattaataaaattattattttgtgtttgtgctattatagtt gagattattattaatgagggtaaataagatgaagataattgcaggtttg ggtaatccgggtcaaaaatatgataagaccaaacataatactggtttcat gacaatggatcactaccttgataaaaaggtttgactttaaataaagata aatttgaagggcattggactaaaaagcttatcgataccgtcgaccgat
```

In some embodiments, a promoter is spaced 0-300 (e.g., 0-100, 10-50 or 20-30) nucleotides upstream from a nucleic acid to which the promoter is operably linked. In some embodiments, a promoter is adjacent to a nucleic acid to which the promoter is operably linked. In some embodiments, a promoter is operably linked to multiple nucleic acids that together transcribe a fusion protein. A fusion protein can comprise any one of the following elements: a secretion signal peptide, a carrier protein, one or more cleavage sites, Ang-(1-7), a hinge and ACE2.

Secretion Signal Peptide

In some embodiments of any one of the polynucleic acids provided herein, a polynucleic acid comprises a nucleic acid encoding a secretion signal peptide. Secretion signal peptides aid the secretion out of a cell of the protein to which the secretion signal peptide is fused or a fusion protein of which it is a part. A secretion signal peptide may be co-translational or post-translational. In some embodiments, a secretion signal peptide is from the usp45 gene of *Lactococcus lactis*, having at least 80%, 85%, 90%, 95%, 96%, 97%, 98%, 99% or 100% sequence identity to the sequence of SEQ ID NO: 8. In some embodiments, a secretion signal peptide shows at least 80%, 85%, 90%, 95%, 96%, 97%, 98%, 99%, 100% or more of the secretion efficiency as that of a secretion signal peptide identified as SEQ ID NO: 8. In some embodiments, a nucleic acid encoding a secretion signal peptide has the sequence SEQ ID NO:2, or is a fragment or variant thereof, having at least 80%, 85%, 90%, 95%, 96%, 97%, 98%, 99% or 100% sequence identity to the sequence of SEQ ID NO: 2.

Non-Limiting Example of a Nucleotide Sequence of Secretion Signal Peptide from the Usp45 Gene of *Lactococcus lactis*:

```
                                         (SEQ ID NO: 2)
atgaaaaaaagattatctcagctattttaatgtctacagtgatactttc tgctgcagccccgttgtcaggtgtttacgctgacacaaactcagat
```

Non-Limiting Example of an Amino Acid Sequence of Secretion Signal Peptide from the Usp45 Gene of *Lactococcus lactis*:

```
                                         (SEQ ID NO: 8)
           MKKKIISAILMSTVILSAAAPLSGVYADTNSD
```

In some embodiments, a nucleic acid encoding a secretion signal peptide lies 5' to a nucleic acid encoding a carrier protein such that the secretion signal peptide is positioned in the N-term of a protein to which it is fused. In some embodiments, a secretion signal peptide is fused to Ang-(1-7). In some embodiments, a secretion signal peptide is part of a fusion protein comprising a carrier protein and Ang-(1-7), that may or may not comprise a cleavage site, or another protein, such as ACE2. In some embodiments, a nucleic acid encoding a secretion signal peptide lies 3' to a nucleic acid encoding a carrier protein such that the secretion signal peptide is positioned between the carrier protein and Ang-(1-7), either before or after the cleavage site. In some embodiments, a nucleic acid encoding a secretion signal peptide lies 3' to a nucleic acid encoding Ang-(1-7) such that the encoded secretion signal peptide is positioned in the C-term of the fusion protein.

Carrier Protein

A carrier protein can help with the delivery of a small peptide (e.g., Ang-(1-7)) in an oral formulation numerous ways. For example, a carrier protein (e.g., B subunit of cholera toxin, CTB) can help to deliver Ang-(1-7) and/or ACE2 to target tissue from the gut by allowing easy transmucosal migration. A carrier protein can also dampen an immune response to administration of a small peptide.

Furthermore, Ang-(1-7) is a peptide of only 7 amino acids (SEQ ID NO: 10). Fusion of Ang-(1-7) to a carrier protein also aids in transcription of the Ang-(1-7).

In some embodiments, a carrier protein in any one of the polynucleic acids described herein is the B subunit of cholera toxin (CTB), or a fragment or variant thereof. In some embodiments, the nucleotide sequence encoding a CTB carrier protein is codon optimized such that it provides maximum or high expression in *Lactobacillus*. In some embodiments, the amino acid sequence of a CTB carrier protein is SEQ ID NO: 14. In some embodiments, a single amino acid change from histidine to alanine is made to the sequence of CTB carrier protein, such that it manifests lower toxicity but provides the same binding to monosialotetrahexosylganglioside (GM1) for transmucosal transport (SEQ ID NOs: 9 and 3). In some embodiments, a nucleic acid encoding a carrier protein has at least 80%, 85%, 90%, 95%, 96%, 97%, 98%, 99% or 100% sequence identity to SEQ ID NO: 3. In some embodiments, a carrier protein has at least 80%, 85%, 90%, 95%, 96%, 97%, 98%, 99% or 100% sequence identity to the sequence of SEQ ID NO: 9. In some embodiments, a carrier protein shows at least 80%, 85%, 90%, 95%, 96%, 97%, 98%, 99%, 100% or more binding activity to GM1 gangliosides and thus at least 80%, 85%, 90%, 95%, 96%, 97%, 98%, 99%, 100% or more transmucosal transport efficiency compared to a carrier protein having a sequence of SEQ ID NO: 9.

Non-Limiting Example of an Amino Acid Sequence of Unmodified CTB

```
                                        (SEQ ID NO: 14)
MIKLKFGVFFTVLLSSAYAHGTPQNITDLCAEYHNTQIHTLNDKIFSYTE

SLAGKREMAIITFKNGATFQVEVPGSQHIDSQKKAIERMKDTLRIAYLTE

AKVEKLCVWNNKTPHAIAAISMAN
```

Non-Limiting Example of an Amino Acid Sequence of Modified CTB

```
                                        (SEQ ID NO: 9)
MIKLKFGVFFTVLLSSAYAHGTPQNITDLCAEYHN

TQIHTLNDKIFSYTESLAGKREMAIITFKNGATFQ

VEVPGSQAIDSQKKAIERMKDTLRIAYLTEAKVEK

LCVWNNKTPHAIAAISMAN
```

Non-Limiting Example of a Nucleic Acid Sequence Encoding Modified CTB

```
                                        (SEQ ID NO: 3)
atgattaagttaaagtttggtgttttttttactgt tttattatcatcagcttacgctcacggtactccac aaaacattactgatttatgtgctgaataccacaac actcaaattcacactttaaacgataagattttttc atacactgaatcattagctggtaagcgtgaaatgg
```

-continued
```
ctattattacttttaagaacggtgctacttttcaa gttgaagttccaggttcacaagctattgattcaca aaagaaggctattgaacgtatgaaggatactttac gtattgcttacttaactgaagctaaggttgaaaag ttatgtgtttggaacaacaagactccacacgctat tgctgctatttcaatggctaac
```

In some embodiments, a carrier protein is cell penetrating peptide (CPP), also known as protein transduction domains (PTDs). CPPs are short peptides, <30 amino acids, possessing cell membrane penetration properties and, when fused with the proteins, can carry those proteins directly into cells [van den Berg A, Dowdy S F: Protein transduction domain delivery of therapeutic macromolecules. Curr Opin Biotechnol 2011, 22(6):888-893]. The mechanisms of CPP-mediated cell entry are different from that of CTB, which is receptor-mediated. In some embodiments, a CPP is derived from Pancreatic And Duodenal Homeobox 1 (PDX-1). In some embodiments, the nucleotide sequence encoding a CPP derived from PDX-1 is codon optimized such that it provides maximum or high expression in *Lactobacillus*. In some embodiments, the amino acid sequence of a CPP derived from PDX-1 is SEQ ID NO: 19. In some embodiments, a nucleic acid encoding a carrier protein has at least 80%, 85%, 90%, 95%, 96%, 97%, 98%, 99% or 100% sequence identity to SEQ ID NO: 18. In some embodiments, a carrier protein has at least 80%, 85%, 90%, 95%, 96%, 97%, 98%, 99% or 100% sequence identity to the sequence of SEQ ID NO: 19. In some embodiments, a carrier protein shows at least 80%, 85%, 90%, 95%, 96%, 97%, 98%, 99%, 100% or cell penetrating activity compared to a carrier protein having a sequence of SEQ ID NO: 19.

Non-Limiting Example of a Nucleic Acid Sequence Encoding a CPP Derived from PDX-1

```
                                        (SEQ ID NO: 18)
cgtcatatcaagatctggttccaaaaccgtcgtatgaagtggaagaag
```

Non-Limiting Example of an Amino Acid Sequence of a CPP Derived from PDX-1

```
                                        (SEQ ID NO: 19)
                    RHIKIWFQNRRMKWKK
```

Ang-(1-7)

In some embodiments, the amino acid sequence of Ang-(1-7) is SEQ ID NO: 10. In some embodiments, Ang-(1-7) has a sequence that comprises SEQ ID NO: 10 and has at least 80%, 85%, 90%, 95%, 96%, 97%, 98%, 99%, 100% or more binding activity to Mas receptor than the peptide of SEQ ID NO: 10. In some embodiments, Ang-(1-7) has a sequence that comprises SEQ ID NO: 10 and has at least 80%, 85%, 90%, 95%, 96%, 97%, 98%, 99%, 100% or more signaling activity through Mas receptor binding compared to the peptide of SEQ ID NO: 10. In some embodiments, a nucleic acid encoding Ang-(1-7) is SEQ ID NO: 4, or a variant thereof. In some embodiments, a nucleic acid encoding Ang-(1-7) has at least 80%, 85%, 90%, 95%, 96%, 97%, 98%, 99% or 100% sequence identity to the sequence of SEQ ID NO: 4.

Non-Limiting Example of an Amino Acid Sequence of Ang-(1-7)

```
                                          (SEQ ID NO: 10)
DRVYIHP
```

Non-Limiting Example of a Nucleic Acid Sequence of Ang-(1-7)

```
                                          (SEQ ID NO: 4)
             gatcgtgtttacattcatcct
```

In some embodiments, embodiments described using Ang-(1-7) in this application can be implemented using other angiotensin peptides (e.g., other fragments of Angiotensin I) or nucleic acids encoding such angiotensin peptides. For example, peptides such as Ang-(1-5), Ang-(1-6), Ang-(1-8), Ang-(1-9), Ang-(2-8), Ang-(3-8), Ang-(2-9), Ang-(3-9), or other angiotensin peptides that differ from these peptides or from Ang-(1-7) by one or two amino acid deletions, substitutions, and/or additions, and/or by the addition of 3-50 amino acids (e.g., from an angiotensin polypeptide). In some embodiments, longer angiotensin (e.g., angiotensin I) peptides (e.g., 50-100, 100-200, or longer, up to a full length angiotensin polypeptide), or nucleic acids encoding such polypeptides can be used. In some embodiments, the angiotensin polypeptides are human angiotensin polypeptides. In some embodiments, the angiotensin polypeptides are non-human angiotensin polypeptides (e.g., from other mammalian species). In some embodiments, angiotensin peptides longer than Ang-(1-7), for example Ang-(1-9), is cleaved by ACE to generate Ang-(1-7) that produces beneficial effects.

In some embodiments, the amino acid sequence of Ang-(1-9) is SEQ ID NO: 20. In some embodiments, Ang-(1-9) has a sequence that comprises SEQ ID NO: 20 and has at least 80%, 85%, 90%, 95%, 96%, 97%, 98%, 99%, 100% or more binding activity to Mas receptor than the peptide of SEQ ID NO: 20. In some embodiments, Ang-(1-9) has a sequence that comprises SEQ ID NO: 20 and has at least 80%, 85%, 90%, 95%, 96%, 97%, 98%, 99%, 100% or more signaling activity through Mas receptor binding compared to the peptide of SEQ ID NO: 20. In some embodiments, corresponding fragments of angiotensin can be combined (e.g., Ang-(1-7), Ang-(3-8), Ang-(1-9) (DRVYIHPFH; SEQ ID NO: 20) and Ang-(1-5).

Non-Limiting Example of an Amino Acid Sequence of Ang-(1-9)

```
                                          SEQ ID NO: 20
DRVYIHPFH;
```

ACE2

In some embodiments, a nucleotide sequence encoding ACE2 is codon optimized such that it provides maximum or high expression in *Lactobacillus*. In some embodiments, the amino acid sequence of ACE2 is SEQ ID NO: 13. In some embodiments, the sequence of ACE2 has at least 80%, 85%, 90%, 95%, 96%, 97%, 98%, 99%, 100% or more enzymatic activity than the protein of SEQ ID NO: 13. In some embodiments, a nucleic acid encoding ACE2 is SEQ ID NO: 7, or a fragment or variant thereof. In some embodiments, a nucleic acid encoding ACE2 has at least 80%, 85%, 90%, 95%, 96%, 97%, 98%, 99% or 100% sequence identity to the sequence of SEQ ID NO: 7.

In some embodiments, ACE2 is fused to a carrier protein without a cleavage site between the ACE2 and carrier protein.

Non-Limiting Example of an Amino Acid Sequence of ACE2

```
                                          (SEQ ID NO: 13)
MSSSSWLLLSLVAVTAAQSTIEEQAKTFLDKFNHE

AEDLFYQSSLASWNYNTNITEENVQNMNNAGDKWS

AFLKEQSTLAQMYPLQEIQNLTVKLQLQALQQNGS

SVLSEDKSKRLNTILNTMSTIYSTGKVCNPDNPQE

CLLLEPGLNEIMANSLDYNERLWAWESWRSEVGKQ

LRPLYEEYVVLKNEMARANHYEDYGDYWRGDYEVN

GVDGYDYSRGQLIEDVEHTFEEIKPLYEHLHAYVR

AKLMNAYPSYISPIGCLPAHLLGDMWGRFWTNLYS

LTVPFGQKPNIDVTDAMVDQAWDAQRIFKEAEKFF

VSVGLPNMTQGFWENSMLTDPGNVQKAVCHPTAWD

LGKGDFRILMCTKVTMDDFLTAHHEMGHIQYDMAY

AAQPFLLRNGANEGFHEAVGEIMSLSAATPKHLKS

IGLLSPDFQEDNETEINFLLKQALTIVGTLPFTYM

LEKWRWMVFKGEIPKDQWMKKWWEMKREIVGVVEP

VPHDETYCDPASLFHVSNDYSFIRYYTRTLYQFQF

QEALCQAAKHEGPLHKCDISNSTEAGQKLFNMLRL

GKSEPWTLALENVVGAKNMNVRPLLNYFEPLFTWL

KDQNKNSFVGWSTDWSPYADQSIKVRISLKSALGD

KAYEWNDNEMYLFRSSVAYAMRQYFLKVKNQMILF

GEEDVRVANLKPRISFNFFVTAPKNVSDIIPRTEV

EKAIRMSRSRINDAFRLNDNSLEFLGIQPTLGPPN

QPPVSIWLIVFGVVMGVIVVGIVILIFTGIRDRKK

KNKARSGENPYASIDISKGENNPGFQNTDDVQTSF
```

Non-Limiting Example of a Nucleic Acid Sequence Encoding ACE2

```
                                          (SEQ ID NO: 7)
atgtcatcatcatcatggttgttgttgtcattggt tgctgttaccgctgctcaatcaaccatcgaagaac aagctaagaccttcttggataagttcaaccatgaa gctgaagatttgttctatcaatcatcattggcttc atggaactataacaccaacatcaccgaagaaaacg ttcaaaacatgaacaacgctggcgataagtggtca
```

-continued

```
gctttcttgaaggaacaatcaaccttggctcaaat
gtatccattgcaagaaatccaaaacttgaccgtta
agttgcaattgcaagctttgcaacaaaacggctca
tcagttttgtcagaagataagtcaaagcgtttgaa
caccatcttgaacaccatgtcaaccatctattcaa
ccggcaaggtttgcaacccagataacccacaagaa
tgcttgttgttggaaccaggcttgaacgaaatcat
ggctaactcattggattataacgaacgtttgtggg
cttgggaatcatggcgttcagaagttggcaagcaa
ttgcgtccattgtatgaagaatatgttgttttgaa
gaacgaaatggctcgtgctaaccattatgaagatt
atggcgattattggcgtggcgattatgaagttaac
ggcgttgatggctatgattattcacgtggccaatt
gatcgaagatgttgaacataccttcgaagaaatca
agccattgtatgaacatttgcatgcttatgttcgt
gctaagttgatgaacgcttatccatcatatatctc
accaatcggctgcttgccagctcatttgttgggcg
atatgtggggccgtttctggaccaacttgtattca
ttgaccgttccattcggccaaaagccaaacatcga
tgttaccgatgctatggttgatcaagcttgggatg
ctcaacgtatcttcaaggaagctgaaaagttcttc
gtttcagttggcttgccaaacatgacccaaggctt
ctgggaaaactcaatgttgaccgatccaggcaacg
ttcaaaaggctgtttgccatccaaccgcttgggat
ttgggcaagggcgatttccgtatcttgatgtgcac
caaggttaccatggatgatttcttgaccgctcatc
atgaaatgggccatatccaatatgatatggcttat
gctgctcaaccattcttgttgcgtaacggcgctaa
cgaaggcttccatgaagctgttggcgaaatcatgt
cattgtcagctgctaccccaaagcatttgaagtca
atcggcttgttgtcaccagatttccaagaagataa
cgaaaccgaaatcaacttcttgttgaagcaagctt
tgaccatcgttggcaccttgccattcacctatatg
ttggaaaagtggcgttggatggttttcaagggcga
aatcccaaaggatcaatggatgaagaagtggtggg
aaatgaagcgtgaaatcgttggcgttgttgaacca
gttccacatgatgaaacctattgcgatccagcttc
attgttccatgtttcaaacgattattcattcatcc
gttattataccccgtaccttgtatcaattccaattc
caagaagctttgtgccaagctgctaagcatgaagg
```

-continued

```
cccattgcataagtgcgatatctcaaactcaaccg
aagctggccaaaagttgttcaacatgttgcgtttg
ggcaagtcagaaccatggaccttggctttggaaaa
cgttgttggcgctaagaacatgaacgttcgtccat
tgttgaactatttcgaaccattgttcacctggttg
aaggatcaaaacaagaactcattcgttggctggtc
aaccgattggtcaccatatgctgatcaatcaatca
aggttcgtatctcattgaagtcagctttgggcgat
aaggcttatgaatggaacgataacgaaatgtattt
gttccgttcatcagttgcttatgctatgcgtcaat
atttcttgaaggttaagaaccaaatgatcttgttc
ggcgaagaagatgttcgtgttgctaacttgaagcc
acgtatctcattcaacttcttcgttaccgctccaa
agaacgtttcagatatcatcccacgtaccgaagtt
gaaaaggctatccgtatgtcacgttcacgtatcaa
cgatgctttccgtttgaacgataactcattggaat
tcttgggcatccaaccaaccttgggcccaccaaac
caaccaccagtttcaatctggttgatcgttttcgg
cgttgttatgggcgttatcgttgttggcatcgtta
tcttgatcttcaccggcatccgtgatcgtaagaag
aagaacaaggctcgttcaggcgaaaacccatatgc
ttcaatcgatatctcaaagggcgaaaacaacccag
gcttccaaaacaccgatgatgttcaaacctcattc
t
```

Cleavage Sites and Hinges

In some embodiments of any one of the polynucleic acids disclosed herein, a nucleic acid encoding a cleavage site lies between the nucleic acids encoding a carrier protein and Ang-(1-7). Such a cleavage site enables cleavage of a fusion protein separating a carrier protein and Ang-(1-7) once the fusion protein is expressed and secreted from a bacterium. In some embodiments, a cleavage site between a carrier protein and Ang-(1-7) is a site recognized by furin (furin cleavage site). In some embodiments, a furin cleavage site is R-X-(R/K)-R'. In some embodiments, a furin cleavage site is SEQ ID NO: 11 or SEQ ID NO: 12, or a variant thereof. A variant of a furin cleavage site has at least 80%, 85%, 90%, 95%, 96%, 97%, 98%, 99%, 100% or more cleavage activity by furin than the protein of SEQ ID NO: 11 or SEQ ID NO: 12. SEQ ID NO: 16 shows the nucleic acid sequence of a non-limiting example of a furin cleavage site.

Non-Limiting Example of an Amino Acid Sequence of Furin Cleavage Site

```
                                        (SEQ ID NO: 11)
SRKKR
```

Amino Acid Sequence of a Variant Furin Cleavage Site

```
                                        (SEQ ID NO: 12)
TRSRKKR
```

Nucleic Acid Sequence of Furin Cleavage Site:

```
                                        (SEQ ID NO: 16)
tca cgt aag aag cgt
```

In some embodiments of any one of the polynucleic acids provided herein, a polynucleic acid further comprises a nucleic acid encoding a hinge. A hinge is a flexible peptide or polypeptide sequence connecting two protein domains that can move with respect to each other. In some embodiments, a nucleic acid encoding a hinge lies between a nucleic acid encoding a carrier protein and a nucleic acid encoding Ang-(1-7). In some embodiments, a nucleic acid encoding a hinge lies 3' to the carrier protein and 5' from nucleic acids encoding a cleavage site and Ang-(1-7). In some embodiments, a nucleic acid encoding a hinge lies 3' to nucleic acids encoding a carrier protein and a cleavage site and 5' to a nucleic acid encoding Ang-(1-7). In some embodiments, a nucleic acid encoding a hinge lies 3' to the carrier protein and 5' from a nucleic acid encoding a cleavage site. In some embodiments, a nucleic acid encoding a hinge lies 3' to the carrier protein and 3' to a nucleic acid encoding a cleavage site. In some embodiments, a nucleic acid encoding a cleavage sequence is flanked on either side by nucleic acids encoding a hinge. The hinges on either side of a cleavage site can have the same sequence, or different sequences. In some embodiments, the size of the hinges on either side of a cleavage sequence is the same, and in some embodiments, the size of the hinges on either side of a cleavage sequence is different.

In some embodiments of any one of the polynucleic acids disclosed herein, a nucleic acid encoding a hinge is 3-90 nucleotides (e.g., 3-24, 3-18, 3-12 or 3-9 nucleotides) in length, such that it encodes a protein sequence that is 1-30 amino acids (e.g., 1-20, 5-10, 1-3, 1-6, 1-4 or 1-3 amino acids) in length. An example of the amino acid sequence of a hinge is GPGP. SEQ ID NO: 15 is a non-limiting example of a sequence of a nucleic acid encoding a hinge. SEQ ID NO: 5 shows a non-limiting example of an amino acid sequence of a hinge and furin cleavage site.

Sequence of a Nucleic Acid Encoding a Non-Limiting Example of a Hinge

```
                                        (SEQ ID NO: 15)
ggt cct ggt cct
```

Amino Acid Sequence of a Non-Limiting Example of a Hinge and Furin Cleavage Site

```
                                        (SEQ ID NO: 5)
GPGPSRKKR
```

Terminator

In some embodiments of any one of the polynucleic acids disclosed herein, a polynucleic acid comprises a terminator. A terminator is a nucleic acid sequence that marks the end of a gene and triggers the end of transcription. In some embodiments, a terminator is a prokaryotic terminator. In some embodiments, a terminator is Rho-dependent. In some embodiments, a terminator is Rho-independent.

In some embodiments, a terminator sequence lies 3' to a nucleic acids that together encode a fusion protein. In some embodiments, a fusion protein comprises a carrier protein and Ang-(1-7). In some embodiments, a fusion protein comprises a carrier protein, a cleavage site and Ang-(1-7). In some embodiments, a fusion protein comprises a carrier protein, a first cleavage site, Ang-(1-7), a second cleavage site and ACE2. In some embodiments, a polynucleic acid that encodes two fusion proteins, one comprising Ang-(1-7) and another comprising ACE2, has two termination sequences. A polynucleic acid encoding two fusion proteins may have termination sequences that are the same or different in sequence.

An example of a termination sequence is provided in SEQ ID NO: 6. In some embodiments, a terminator is a fragment or variant of SEQ ID NO: 6. In some embodiments, a terminator has at least 80%, 85%, 90%, 95%, 96%, 97%, 98%, 99% or 100% sequence identity to the sequence of SEQ ID NO: 6.

Non-Limiting Example of a Terminator Sequence

```
                                        (SEQ ID NO: 6)
gtaattctcatgtttgacagcttatcatcgataag ctttaatgcggtagtttatcacagttaaattgcta acgcagtcaggcaccgtgtatgaaatctaacaatg cgctcatcgtcatcctcggcaccgtcaccctggat gctgtaggcataggcttggttatgccggtactgcc gggcctcttgcgggatatcgtccattccgacagca tcgccagtcactatggcgtgctgctagcgctatat gcgttgatgcaatttctatgcgcacccgttctcgg agcactgtccgaccgctttggccgccgcccagtcc tgctcgcttcgctacttggagccactatcgactac gcgatcatggcgaccacacccgtcctgtggatcc
```

Detection Protein

In some embodiments of any one of the polynucleic acids disclosed herein comprises a nucleic acid encoding a detectable molecule. A detectable molecule is a molecule that can be visualized (e.g., using a naked eye or under a microscope). In some embodiments, a polynucleic acid encodes a detectable molecule such that the detectable molecule is fused to Ang-(1-7), allowing detection of Ang-(1-7) after it is expressed and secreted from a bacterium. In some embodiments, a polynucleic acid comprises a nucleic acid encoding a detectable marker such that it is not fused to another protein encoded from polynucleic acid, but serves as a marker for transformation of the polynucleic acid into a bacterium.

In some embodiments, a detectable molecule is a fluorescent protein, a bioluminescent protein, or a protein that provides color (e.g., β-galactosidase, β-lactamasses, β-glucuronidase and spheriodenone). In some embodiments, a detectable molecule is a fluorescent, bioluminescent or enzymatic protein or functional peptide or functional polypeptide thereof.

In some embodiments, fluorescent protein is a blue fluorescent protein, a cyan fluorescent protein, a green fluorescent protein, a yellow fluorescent protein, an orange fluorescent protein, a red fluorescent protein, or functional peptides or polypeptides thereof. A blue fluorescent protein may be azurite, EBFP, EBFP2, mTagBFP, or Y66H. A cyan fluorescent protein may be ECFP, AmCyan1, Cerulean, CyPet, mECFP, Midori-ishi Cyan, mTFP1, or TagCFP. A Green fluorescent protein may be AcGFP, Azami Green, EGFP, Emarald, GFP or a mutated form of GFP (e.g., GFP-S65T, mWasabi, Stemmer, Superfolder GFP, TagGFP, TurboGFP, and ZsGreen). A yellow fluorescent protein may be EYFP, mBanana, mCitrine, PhiYFp, TagYFP, Topaz, Venus, YPet, or ZsYellow1. An orange fluorescent protein may be DsRed, RFP, DsRed2, DsRed-Express, Ds-Red-monomer, Tomato, tdTomato, Kusabira Orange, mKO2, mOrange, mOrange2, mTangerine, TagRFP, or TagRFP-T. A red fluorescent protein may be AQ142, AsRed2, dKeima-Tandem, HcRed1, tHcRed, Jred, mApple, mCherry, mPlum, mRasberry, mRFP1, mRuby or mStrawberry.

In some embodiments, a detectable marker is a bioluminescent protein, or functional peptide or polypeptide thereof. Non-limiting examples of bioluminescent proteins are firefly luciferase, click-beetle luciferase, *Renilla* luciferase, or luciferase from *Oplophorus gracilirostris*.

In some embodiments, a detectable marker may be any polypeptide or protein that can be detected using methods known in the art. Non-limiting methods of detection are fluorescence imaging, luminescent imaging, bright filed imaging.

Polynucleic Acids Encoding Ang-(1-7) and ACE2

In some embodiments, a polynucleic acid comprises a second set of nucleic acids that encode a second secretion signal peptide, a second carrier protein, a second cleavage site and Ang-(1-7) or ACE2, such that the polynucleic acid encodes two fusion proteins, one comprising ANG-(1-7) and the other comprising ACE2. In some embodiments, a polynucleic acid comprises a nucleic acid encoding a secretion signal peptide, and nucleic acids encoding a first carrier protein, a first cleavage site, Ang-(1-7), a second cleavage site, a second carrier protein, a third cleavage site, and ACE2. Such a polynucleic acid encodes a fusion protein comprising a first carrier protein, a first cleavage site, Ang-(1-7), a second cleavage site, a second carrier protein, a third cleavage site, and ACE2, which once secreted, may be cleaved to form one or more of the following proteins: (1) a first fusion protein comprising a secretory signal peptide, a first carrier protein and Ang-(1-7), (2) a second fusion protein comprising a second carrier protein and ACE2, (3) a first carrier protein, (4) a second carrier protein, (5) Ang-(1-7), and (6) ACE2. In some embodiments, a first fusion protein comprises ACE2 and a second fusion protein comprises Ang-(1-7). In some embodiments, a first carrier protein and a second carrier protein are the same. In some embodiments, all the nucleic acids encoding a cleavage site in a polyncleotide are the same. In some embodiments, two out of three nucleic acids encoding cleavage sites are the same.

Expression Vectors

Provided herein are also expression vectors for expressing Ang-(1-7) in a bacterium. An expression vector for expressing Ang-(1-7) in a bacterium, as disclosed herein, comprises any one of the polynucleic acids discloses herein. In some embodiments, an expression vector is a double-stranded construct that may be circular (e.g., a plasmid). In some embodiments, an expression vector comprises any one of the polynucleic acids disclosed herein. In some embodiments, an expression vector for expressing Ang-(1-7) in a bacterium comprises more than one of any of the polynulceic acids provided herein.

In some embodiments, in addition to any one of the polynucleic acids described above, an expression vector as disclosed herein can comprise one or more of the following elements: an origin of replication, a translation initiation sequence, and an antibiotic resistant genes. In some embodiments, antibiotic resistant genes include, but are not limited to: kanamycin, spectinomycin, streptomycin, ampicillin, carbenicillin, bleomycin, erythromycin, polymyxin B, tetracycline, and chloramphenicol. Compositions described herein may include one or more antibiotic resistant genes.

In some embodiments, an expression vector for the expression of and secretion from a bacterium is designed for food grade production. Such an expression vector may exclude antibiotic resistant genes and an origin of replication (e.g., an integration vector to express Ang-(1-7) for *Lactobacillus* genome). In some embodiments, any one of the expression vectors disclosed herein comprises antibiotic resistant genes that are approved by the FDA (e.g., nisin gene as a selective marker). Nisin is a natural antibacterial peptide produced by *Lactococcus lactis* that is used as a food preservative, and is approved as an additive for food use in the USA. It is commonly used in processed cheese, meats, beverages, etc. during production to extend shelf life by suppressing gram-positive spoilage and growth of pathogenic bacteria.

Genetically Engineered Bacterium and Probiotic Compositions

Disclosed herein is a bacterium that is genetically modified by transformation of any of the expression vectors described herein into a bacterium. In some embodiments, a genetically engineered bacterium is a probiotic or a commensal bacterium with respect to the gut of a subject (e.g., a human gut). A probiotic is any bacterium that provides a health benefit when consumed. A commensal bacterium is one that shares a symbiotic relationship with its host (e.g., gut of a human or other mammalian subject). A genetically modified bacterium, as provided herein, comprises any one of the expression vectors described herein. In some embodiments, a genetically modified bacterium comprises more than one of the expression vectors disclosed herein. In some embodiments, a genetically engineered bacterium comprises more than one of any of the expression vectors disclosed herein. For example, a bacterium may comprise a first expression vector encoding Ang-(1-7) fused to a carrier protein and a second expression vector encoding ACE2.

In some embodiments, a probiotic bacterium is a *Lactobacillus*. In some embodiments, a *Lactobacillus* is *L. paracasei, L. plantarum* or *L. gasseri*.

Provided herein is also a probiotic composition for oral administration comprising a plurality of any one of the genetically engineered bacterium described herein. In some embodiments, a composition comprises more than one genetically engineered bacteria. For example, a probiotic composition may comprise a plurality of bacterium able to express Ang-(1-7) fused to a carrier protein and a plurality of bacterium able to express ACE2 fused to a carrier protein.

In some embodiments, a probiotic composition is in the form of a liquid concentration in which bacterium are alive. Such a composition is stored at a temperature between 1-60° C. (e.g., 1-8° C., 2-10° C., 10-60° C. or 20-40° C.). In some embodiments, a probiotic composition is in the form of a frozen liquid composition in which the bacterium are kept alive by use of a cryoprotectant. Methods for storing bacterial stocks under freezing conditions are known in the art. In some embodiments, a frozen liquid composition does not comprise a cryoprotectant. In some embodiments, bacteria are lyophilized and stored in either powder form or tablet form. Such a composition can be dissolved in a liquid (e.g., water, fruit juice or milk) before oral consumption. In some embodiments, a probiotic composition in tablet form can be administered to a subject orally by swallowing, e.g., with a liquid. In some embodiments, a composition comprises a capsule (e.g., a gel capsule) comprising live bacterium. Such a capsule may be swallowed like a tablet.

A Method of Treating a Disease or Condition Involving RAS

Any one of the probiotic compositions of genetically engineered bacteria able to express and secrete Ang-(1-7) may be orally administered to a subject to treat a disease or condition that involves the RAS. Accordingly, provided herein is a method of treating a disease or condition involving the RAS. Such a method may comprise administering orally to a subject in need thereof a therapeutically effective dose of any one of the probiotic compositions disclosed herein.

In some embodiments, "administering" or "administration" means providing a material to a subject, e.g., in a manner that is pharmacologically useful.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. A therapeutically effective amount of a probiotic compositions comprising bacterium expressing and secreting Ang-(1-7) may be an amount that is capable of delivering an amount of Ang-(1-7) to target tissues such that any one disease symptom is reduced or disease pathology is reduced. As is well known in the medical and veterinary arts, dosage for any one subject depends on many factors, including the subject's size, body surface area, age, the particular composition to be administered, the active ingredient(s) in the composition and concentrations thereof, time of administration, general health, and other drugs being administered concurrently.

Aspects of the disclosure relate to methods for use with a subject, such as human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other non-limiting examples of subjects include domesticated animals such as dogs and cats; livestock such as horses, cattle, pigs, sheep, goats, and chickens; and other animals such as mice, rats, guinea pigs, and hamsters.

In some embodiments, a disease or condition that involves the RAS is a disease or condition that involves RAS dysregulation or dysfunction, or is a disease or condition in which the disease progression, pathology or any one symptom is affected by the RAS. Non-limiting examples of diseases or conditions that involve RAS are pulmonary hypertension, diabetes, diabetes-associated complications, or ocular inflammatory disease. In some embodiments, a diabetes-associated complication is diabetic nephropathy or diabetic retinopathy. In some embodiments, an ocular inflammatory disease is scleritis or uveitis. Uveitis can be anterior, intermediate or posterior uveitis (e.g., choroiditis, retinal vasculitis, retinitis, neuroretinitis, retinochoroiditis or chorioretinitis). In some embodiments, oral administration of *Lactobacillus paracasei*-Ang-(1-7) improves diabetes and its associated renal and/or retinal complications.

Subjects with any of several age-related neurodegenerative diseases such as age-related macular degeneration, Alzheimer's diseases, and Parkinson diseases, may be treated with any of the probiotic compositions disclosed herein. Other examples of diseases and conditions involving the RAS are nephropathy (e.g., that unrelated to diabetes), obesity, a metabolic disease (e.g., diabetes or insulin resistance), and cardiovascular disease (e.g., hypertension, heart failure, coronary artery diseases or atherosclerosis).

In some embodiments, oral delivery of probiotics expressing Ang-(1-7) improves glucose tolerance and/or insulin sensitivity. In some embodiments, oral administration of *Lactobacillus paracasei*-Ang-(1-7) prevents diabetes-induced destruction of insulin producing cells and/or increases insulin levels. In some embodiments, oral delivery of LP-A alleviates the damage in kidney. In some embodiments, oral administration of LP-A prevent diabetes-induced retinal capillary loss. In some embodiments, oral administration of *L. paracasei*-Ang-(1-7) reduce diabetes-induced retinal ganglion cell loss, gliosis and expression of inflammatory cytokines in diabetic retina. In some embodiments, oral administration of *Lactobacillus paracasei*-Ang-(1-7) prevents experimental autoimmune uveitis (EAU). In some embodiments, lyophilized wild-type (WT) *Lactobacillus paracasei* (LP) or LP expressing Ang-(1-7) bacteria are viable and show extend colonization.

In some embodiments, any one of the methods of treating a disease or condition involving the RAS further comprises administering to a therapeutic that is the standard of care for the disease or condition. In some embodiments, a method of treating a disease or condition involving the RAS comprises administering an activator of ACE2 in addition to any one of the probiotic compositions disclosed herein. ACE2 activators are known in the art. US 20120142723 A1 describes small molecule ACE2 activators, and is herein incorporated by reference in its entirety.

A standard of care therapeutic or ACE2 activator can be administered either simultaneously or before or after administration of a probiotic composition. In some embodiments, a probiotic composition comprising genetically modified bacterium expressing and secreting Ang-(1-7) is administered to a subject once a day, or twice a day. In some embodiments, a probiotic composition is administered only during a flare of symptoms. In some embodiments, a probiotic composition as disclosed herein is administered chronically even if a subject does not experience a flare of symptoms.

It is to be understood that the disclosed polynucleic acids, expression vectors, probiotic compositions and methods to treat a disease can be used to deliver any peptide other than Ang-(1-7), or any protein other than ACE2. The polynucleic acids, expression vectors, probiotic compositions and methods to treat a disease is particularly useful for delivering short peptides, e.g., peptides that are 3-10, 5-10, 10-20, 20-30, 30-40 or 40-50 amino acids long. However, the disclosure is useful for the delivery of any protein that is to be delivered via the oral route (e.g., an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic protein, a nuclease or other protein used for gene editing, an Fc-fusion protein or an anticoagulant).

In some embodiments, a therapeutic composition comprising an effective amount of a probiotic bacterial preparation is provided along with a pharmaceutically acceptable carrier. The therapeutic composition can be for human or veterinary use.

In certain embodiments, compositions are suitable for oral administration to a subject. In other embodiments, compositions may be specially formulated for administration in solid or liquid form, including but not limited to those adapted for oral administration, for example, drenches (aqueous or non-aqueous solutions or suspensions), tablets, boluses, powders, granules, pastes; or as an aerosol, for example, as an aqueous aerosol, or other preparation (e.g., liposomal preparation or solid particles) containing the probiotic bacteria.

The phrase "pharmaceutically acceptable" refers to those compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient.

Compositions may conveniently be presented in unit dosage form and may be prepared by any methods well known in the art. The amount of active material which can be combined with a carrier material to produce a single dosage form will vary depending upon the host being treated, the particular mode of administration. The amount of active material which can be combined with a carrier material to produce a single dosage form will generally be that amount of the material which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

In some embodiments, bacterial compositions may be provided as freeze-dried lyophilized powders, and/or formulated into cachets, pills, tablets, lozenges, granules, dragees, capsules, or as a solution or a suspension in an aqueous or non-aqueous liquid, or as an oil-in-water or water-in-oil liquid emulsion, or as an elixir or syrup, or as pastilles (e.g., using an inert base, such as gelatin and glycerin, or sucrose and acacia). A composition also may be administered as a bolus, electuary or paste. Compositions described herein can also include color additives. In some embodiments, compositions may be mixed with a food (e.g., a yogurt or other dairy product) for ingestion by a subject.

Tablets, and other solid dosage forms of the therapeutic compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active material therein.

Liquid dosage forms for oral administration of probiotic bacterial compositions described in this application can include pharmaceutically-acceptable emulsions, microemulsions, solutions, suspensions, syrups and elixirs. In addition, the liquid dosage forms may contain inert diluents commonly used in the art.

In some embodiments, solid or liquid dosage forms do not include agents that inactivate or kill the probiotic bacteria.

Bacterial compositions can be prepared by growing bacteria according to the application in a variety of media, including rich or minimal media. Media can be supplemented with various additional components, including sugar sources. Some non-limiting examples of supplemental components include glucose, amino acids, antibiotics and ATCC Trace Mineral Supplement. Liquid and/or solid cultures used to grow cells associated with the invention can be housed in any of the culture vessels known and used in the art.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Construction of a Shuttle Vector to Express Secreted Ang-(1-7) in *Lactobacillus* and Analysis of Bioavailability of Ang-(1-7)

The Vector

Figures 1, 2:
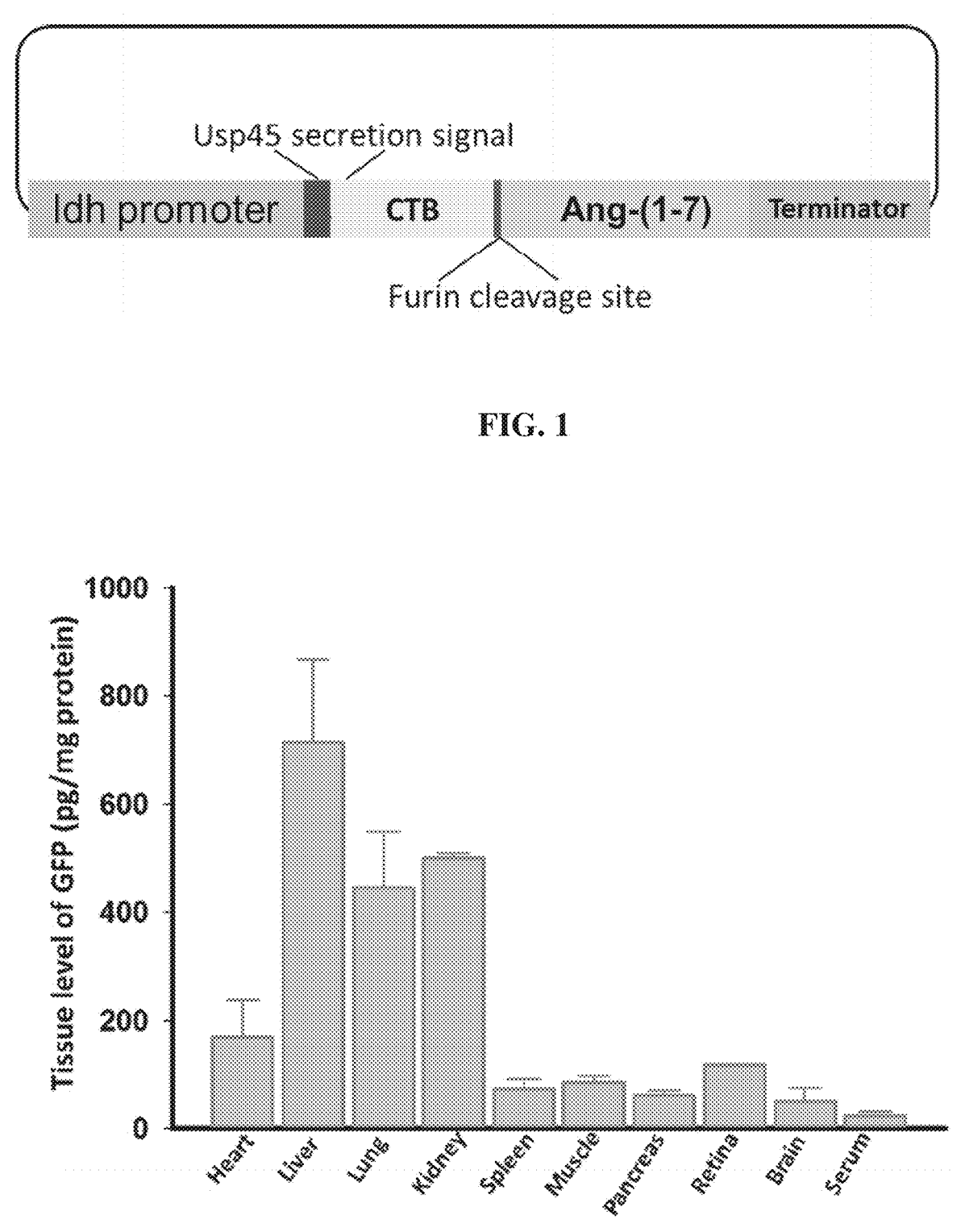

As shown in the diagram of FIG. 1, the shuttle vector contained a promoter and a terminator for reporter and therapeutic gene expression.

The backbone shuttle plasmid containing a GFP reporter gene driven by the lactate dehydrogenase (ldh) promoter from *Lactococcus lactis* was purchased from Addgene (Plasmid #27167) [38]. Ldh is a strong promoter functioning in different bacterial hosts including *E. coli*.

A synthetic gene construct was made to replace the original GFP reporter gene. This gene construct contained the following components:

(1) A secretion signal peptide sequence from usp45 gene of *Lactococcus lactis*, which was slightly modified from Kajikawa et al.[39]. The sequence of the signal peptide is SEQ ID NO: 8.

(2) A transmucosal carrier using modified CTB (SEQ ID NO: 3). The nucleic acid encoding the modified mutant CTB was codon optimized to achieve highest expression level in *Lactobacillus* and a single amino acid change from histidine (H) to alanine (A) (underlined bold) to reduce toxicity without affecting its affinity of monosialotetrahexosylganglioside 1 (GM1) binding [40, 41]. See SEQ ID NO: 9.

(3). A hinge and furin cleavage site between the CTB and Ang-(1-7) to separate the fusion protein comprising the CTB and Ang-(1-7). This hinge and cleavage site was codon optimized for expression in *lactobacillus* (SEQ ID NO: 5).

(4) Ang-(1-7) coding sequence (SEQ ID NO: 4). As a control, a synthetic GFP construct was also made to allow expression and secretion of GFP into circulation.

(5). A stop codon and terminator sequence from the original vector (SEQ ID NO: 6).

All protein/peptide coding sequences are optimized for highest expression level in *Lactobacillus*.

Characterization of In Vivo Expression of a Reporter and Ang-(1-7) in Mice Orally Fed with *Lactobacillus* Expressing a Reporter and Ang-(1-7)

The expression of fusion proteins (CTB-Ang-1-7 and CTB-GFP) in *Lactobacillus* strains was confirmed by western blotting (data not shown). The ability of these probiotics-expressed proteins to deliver the expressed protein into circulation and different tissues following oral administration in mice was evaluated by ELISA. Six week old mice were orally fed with either *L. paracasei*-GFP or *L. paracasei*-Ang-(1-7) at $1 \times 10^{10}$ CFU/mouse daily for 5 days. Mice were then sacrificed and serum and tissue samples were collected. GFP concentration in tissues was measured by enzyme-linked immunosorbent assay. Ang-(1-7) levels were determined by a commercial EIA kit (Bachem, San Carlos, Calif.). As shown in FIG. 2, GFP is efficiently expressed, secreted and taken up by different tissues. When tested in different probiotic strains, it was found that Ang-(1-7) is also efficiently expressed and secreted into circulation in three probiotic strains (FIG. 3).

Summary of Results

The results described above showed that oral delivery of Ang-(1-7) using probiotic bacteria genetically engineered to express and secrete Ang-(1-7) effectively delivers Ang-(1-7) to circulation and target tissue.

Example 2: Efficacy of Orally Administered Probiotic Bacteria Genetically Engineered to Express and Secrete Ang-(1-7) in Pulmonary Hypertension Previous studies by the inventors have established that activation of the members of the vasoprotective axis of RAS, ACE2 or Ang-(1-7), prevents and arrests progression of pulmonary hypertension (PH) pathophysiology.

Oral Administration of *Lactobacillus paracasei* (LP) Genetically Engineered to Express and Secrete Ang-(1-7) [LP-A] Prevents Monocrotaline (MCT)-Induced Pulmonary Hypertension (PH).

Figure 5:
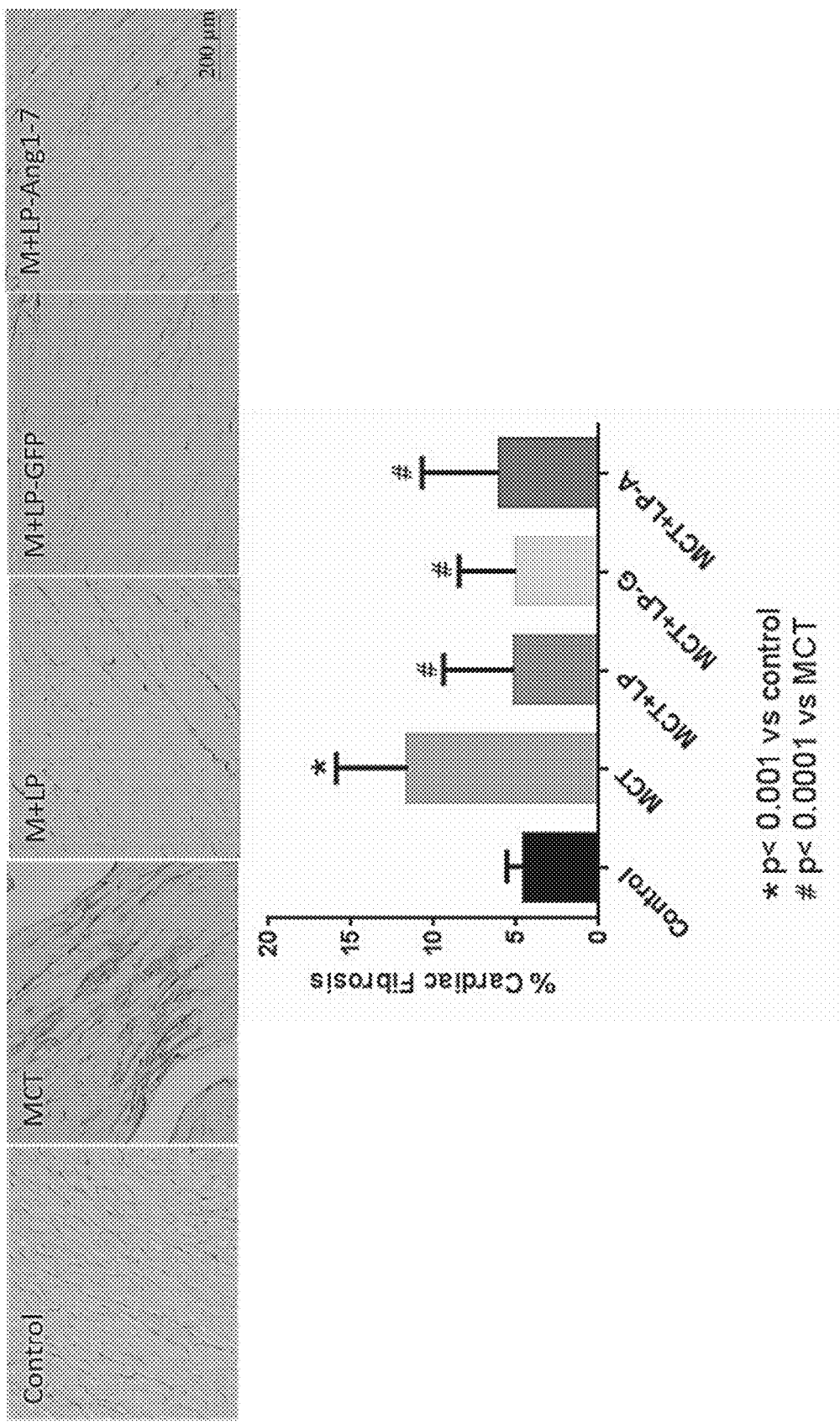
FIG. 5 shows that oral administration of LP, LP-G and LP-A exerts antifibrotic effects and prevents MCP-induced increase of interstitial collagen deposition in the right ventricle. Data shown are mean±SEM. *p<0.001 vs control rats and #p<0.0001 vs MCT rats. N=6 to 8 animals/group.
Figure 6A:
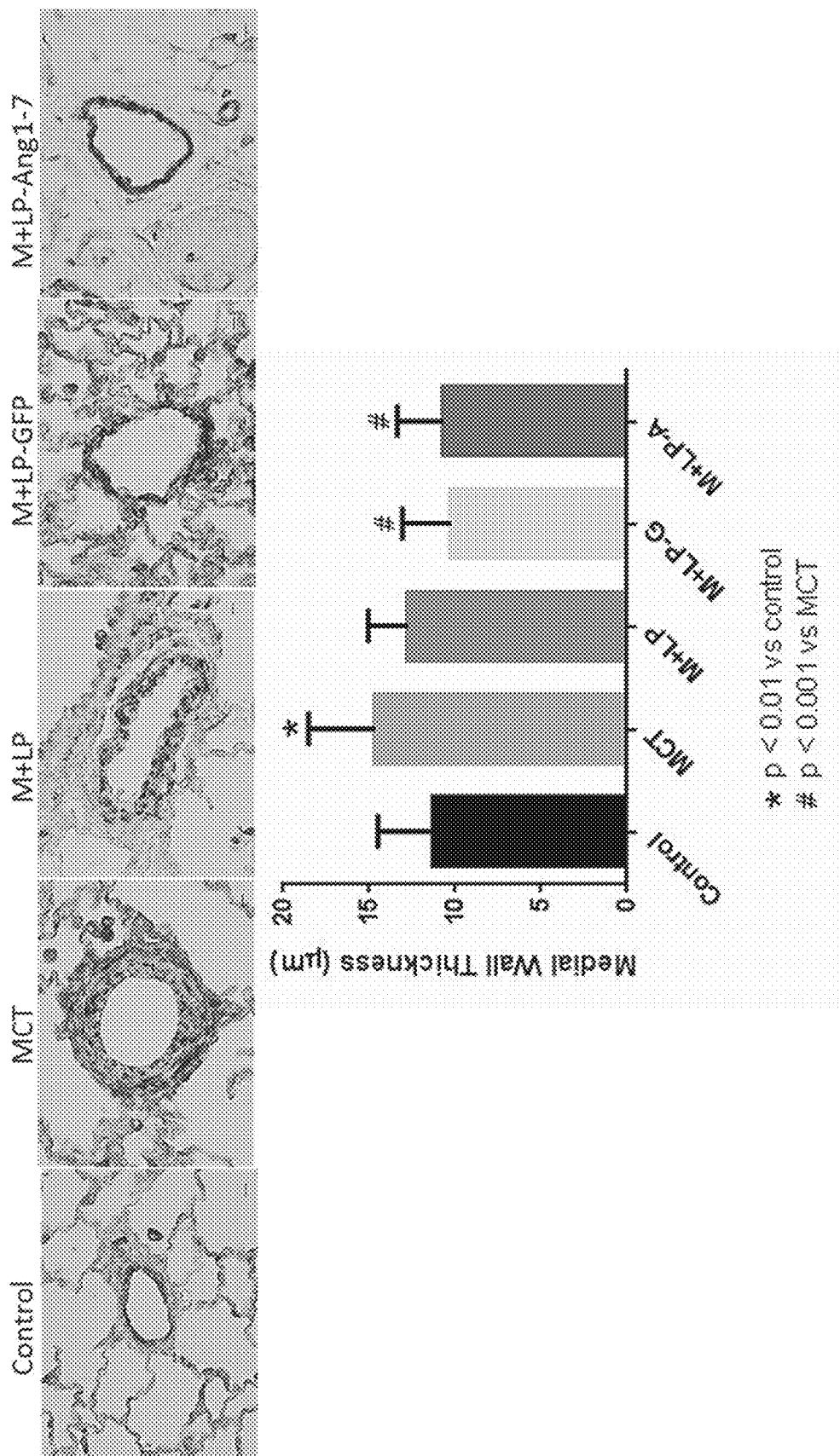
FIG. 6A shows that oral administration of LP-G and LP-A restores medial wall thickness of the pulmonary arteries to control levels in rats, measured by staining for α-smooth muscle actin. Scale bar, 50 m. Data shown are mean±SEM. *p<0.05 vs control rats, #p<0.05 vs MCT rats, $p<0.05 vs MCT+LP rats. N=6 to 8 animals/group.

To test whether oral administration of probiotic-expressed Ang-(1-7) would provide cardiopulmonary protection against PH, the monocrotaline (MCT)-induced PH rat model was used. PH was induced by injecting MCT (50 mg/Kg s.c) in rats. A subset of animals was orally gavaged every other day for four weeks with $1 \times 10^9$ CFU of either *Lactobacillus paracasei* (LP), LP secreting GFP (LP-GFP), or LP secreting Ang-(1-7) (LP-A). Results of these studies are shown in FIGS. 4A-D. It was observed that oral feeding of LP-A significantly reduced MCT-induced right ventricular systolic pressure (RVSP) by 43% (Control: 27±1; MCT: 76±8; MCT+LP: 56+6; MCT+LP-GFP: 59+7; MCT+LP-A: 43±3 mmHg) and RV hypertrophy by 33% (Control: 0.25±0.01; MCT: 0.6+0.02; MCT+LP: 0.48+0.04; MCT+LP-GFP: 0.48+0.04; MCT+LP-A: 0.41+0.03) (FIGS. 4A-4D). Moreover, LP-A feeding restored cardiac functions and attenuated myocardial fibrosis (FIG. 5 and FIG. 6A). Feeding of LP-A was repeated two more times and its beneficial effects on pulmonary and cardiac pathophysiology associated with PH were confirmed in the MCT rat model.

Figure 6B:
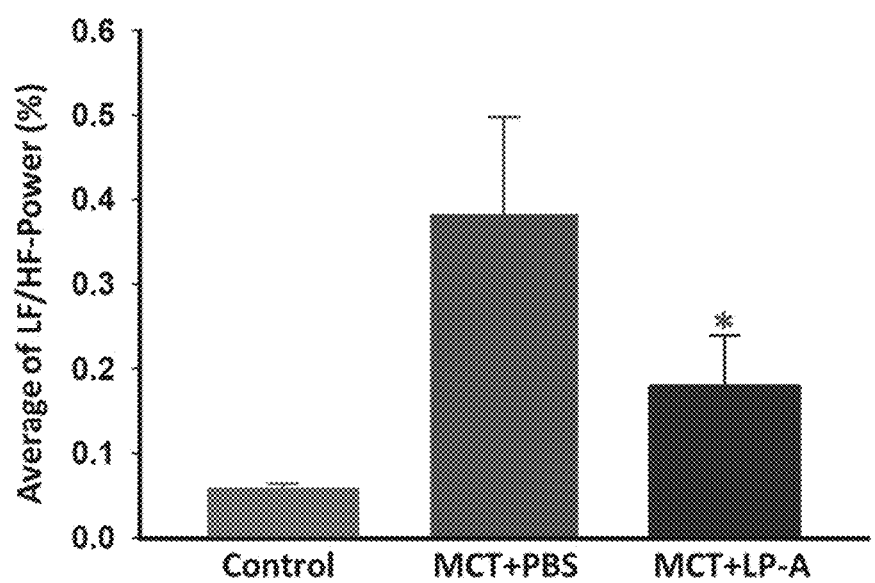
FIG. 6B shows that the ratio of the powers in the low- (LF) and high-frequency (HF) bands in heart rate variability frequency bands, known as LF-HF ratio (LF/HF), in control, MCT rats treated with PBS and LP-A. N=6/group. *p<0.05.

Studies have shown an increase in sympathetic nervous system activity in PH. Low frequency (LF) and high frequency (HF) ratio, an index of sympathetic and parasympathetic activities, was measured in MCT-treated rats to determine the effect of oral feeding of LP-A. FIG. 6B shows that there is increase in LF/HF ratio in PH animals compared to control animals, this was significantly attenuated in PH animals treated with LP-A. This data confirms a beneficial effect on autonomic nervous system.

Oral Administration of *Lactobacillus paracasei* (LP) or LP-Ang-(1-7) (LP-A) Prevents MCT-Induced Gut Dysbiosis.

Figure 7:
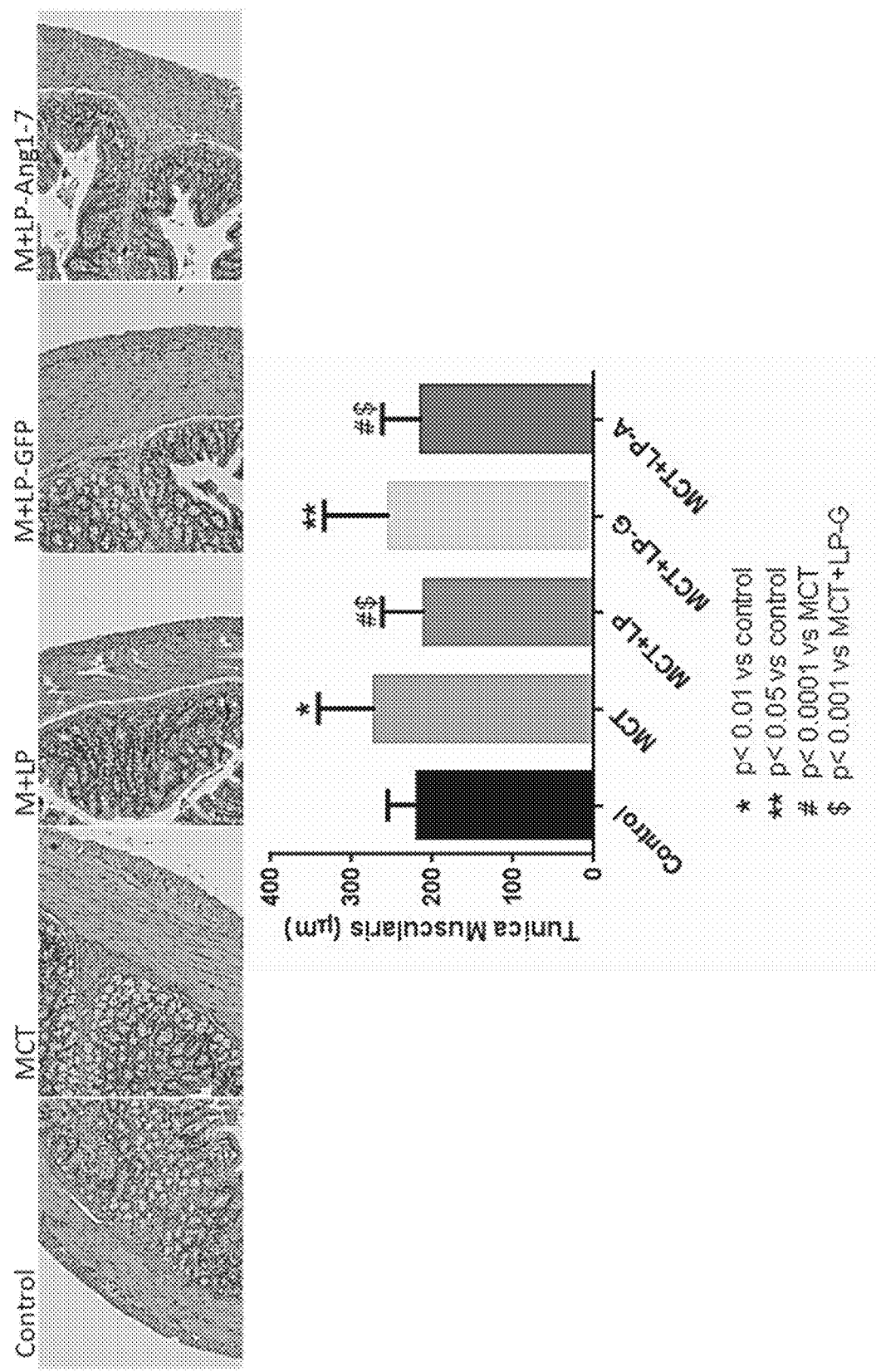
FIG. 7 shows that oral administration of LP or LP-A prevents thickening of the muscularis layer of the proximal colon. Data shown are mean±SEM. *p<0.01 vs control rats, **p<0.001 vs control rats, #p<0.0001 vs MCT rats, $p<0.001 vs MCT+LP-G rats. N=6 to 8 animals/group.
Figure 8:
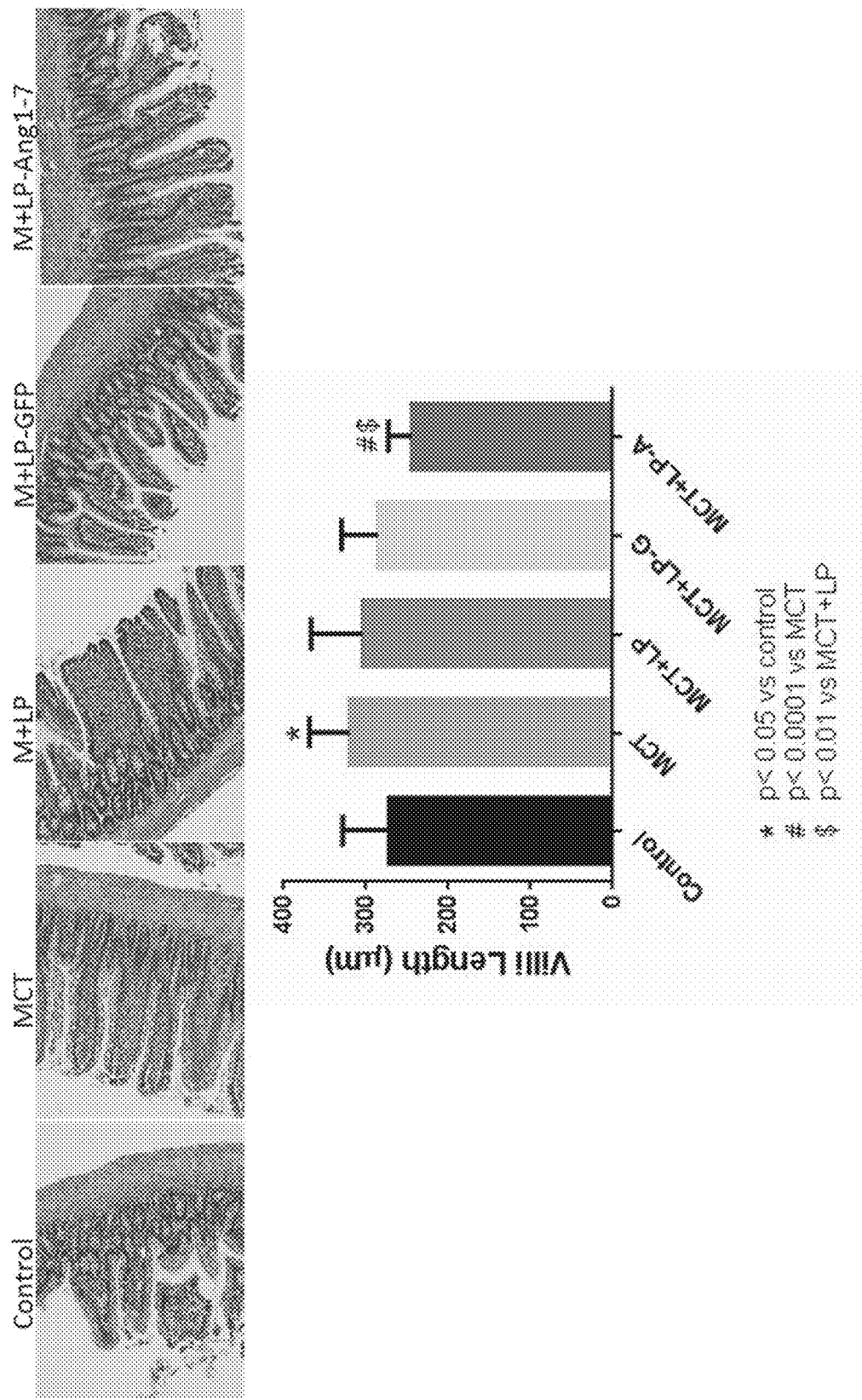
FIG. 8 shows that oral administration of *Lactobacillus paracasei*-Ang-(1-7) (LP-A) prevents the MCT-induced increase in villi length of the small intestine. Data shown are mean±SEM. *p<0.01 vs control rats, #p<0.0001 vs MCT rats, $p<0.01 vs MCT+LP rats. N=6 to 8 animals/group.
Figure 9:
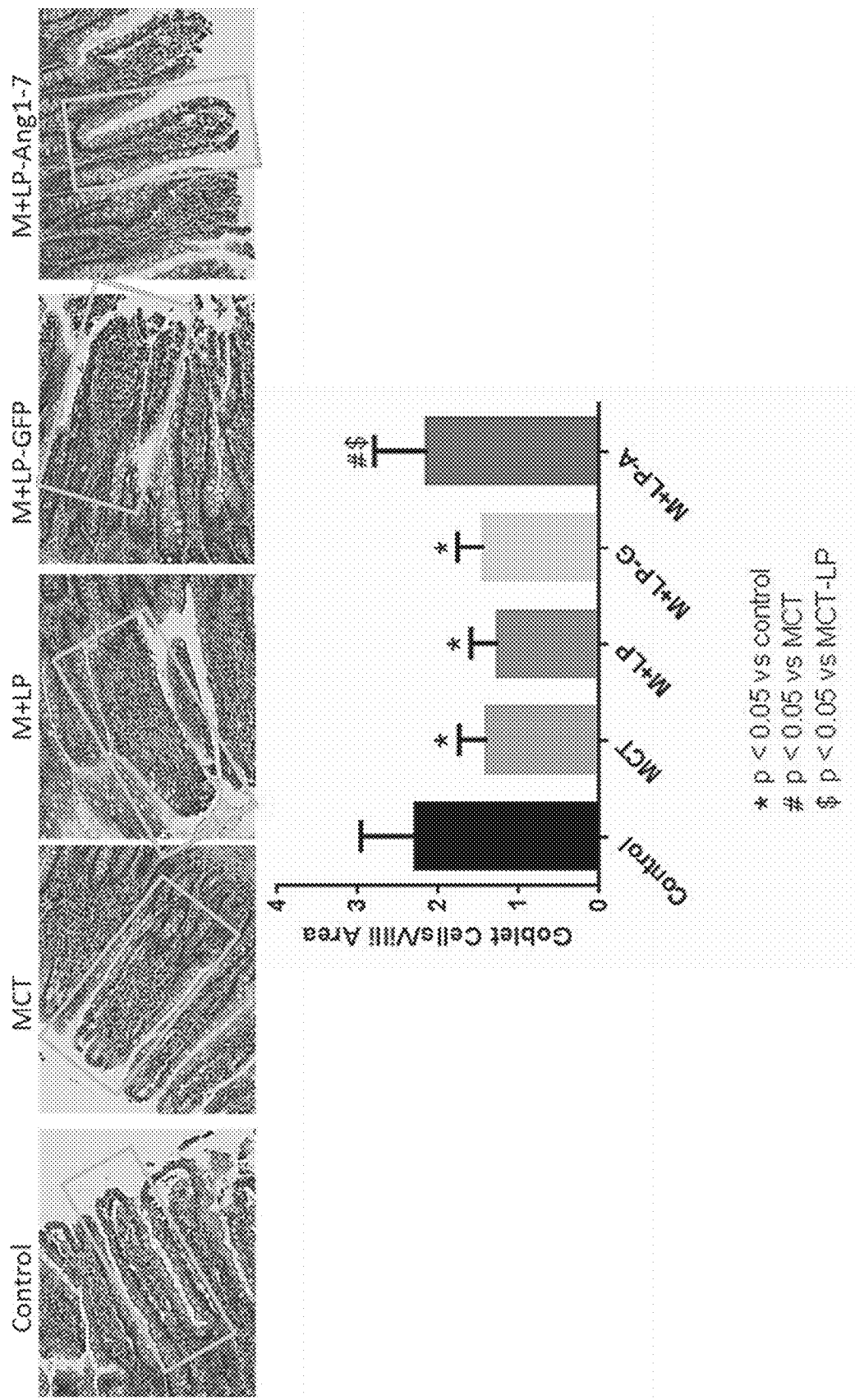
FIG. 9 shows that oral administration of LP-A restores the number of goblet cells per villi area in the small intestine to control levels in rats. Data shown are mean±SEM. *p<0.05 vs control rats, #p<0.05 vs MCT rats, $p<0.05 vs MCT+LP rats. N=6 to 8 animals/group.

MCT-induced PH was associated with an increase in ileum villus length and thickening of proximal colon, and a decrease in goblet cells/villus area, all of which indicate intestinal injury and altered immune status. However, these parameters were significantly attenuated by oral feeding of LP or LP-A (FIGS. 7-9).

Summary of Results

These results demonstrate that oral administration of a genetically modified commensal bacterium that can secrete Ang-(1-7) provides cardiopulmonary protection against experimental PH. The engineered probiotic reduced blood pressure, improved heart contractility and reduced heart wall thickness.

Example 3: Efficacy of Orally Administered Probiotic Bacteria Genetically Engineered to Express and Secrete Ang-(1-7) in Diabetes and Diabetic Complications The beneficial effects of Ang-(1-7) in metabolic diseases including diabetes and its associated complications are well known [7, 9, 42]. Previous studies by the inventors using viral vectors for local ocular gene delivery demonstrated protective effects against diabetes-induced retinopathy in animal models [16].

Oral Administration of *Lactobacillus* LP-A Prevents Streptozotocin (STZ)-Induced Destruction of Insulin Producing Cells, Increases Insulin Sensitivity and Glucose Tolerance, and Diabetes-Induced Nephropathy and Retinopathy in Diabetic Mice.

Figure 10F:
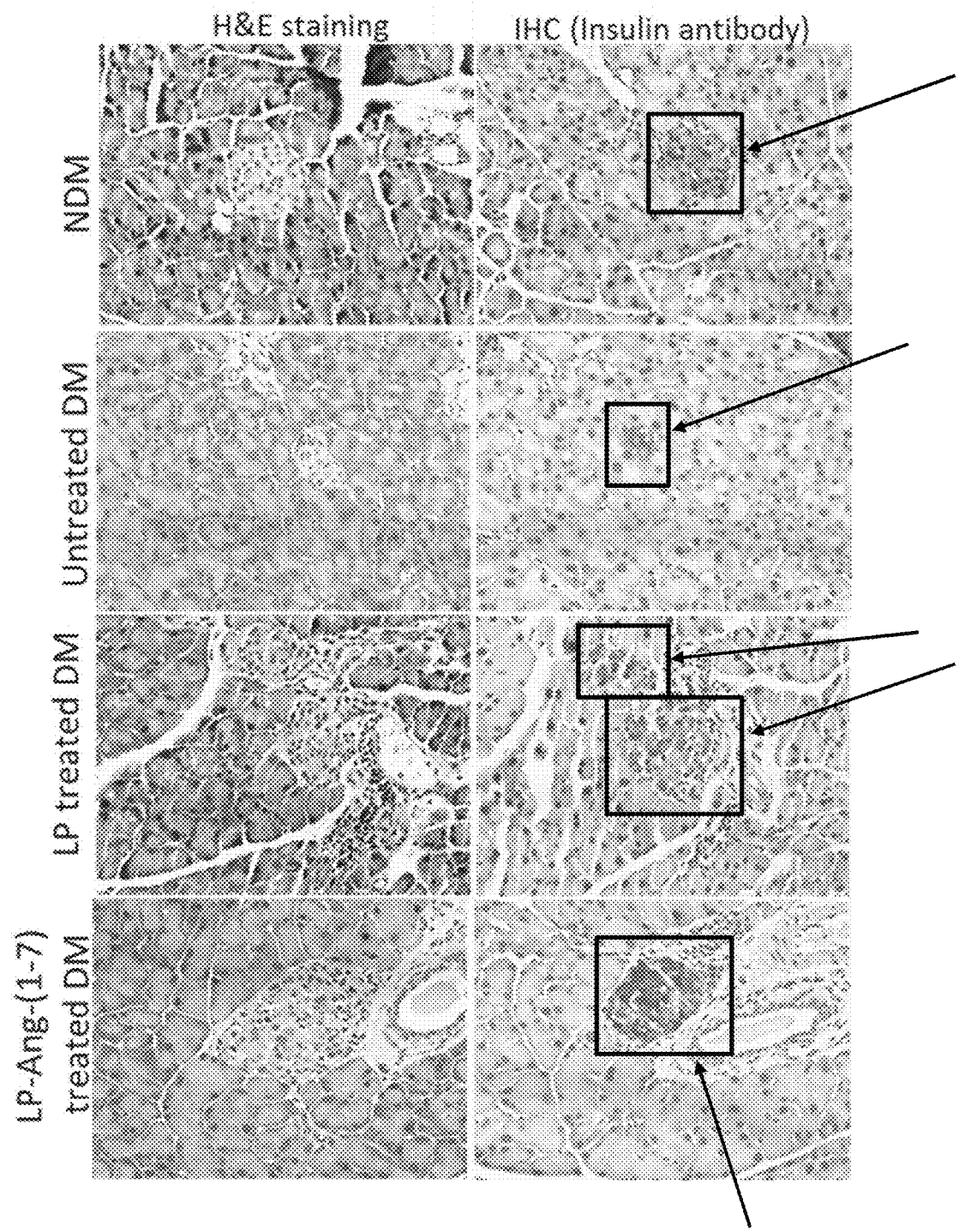
FIG. 10F shows oral administration of *Lactobacillus paracasei* (LP) alone and LP-Ang-(1-7) improved STZ-induced damage to insulin producing beta cells in pancreas, improved structure and morphology of islets (illustrated within the box indicated by an arrow) and increased insulin expression in diabetic eNOS−/− mice. N=4.
Figure 11A:
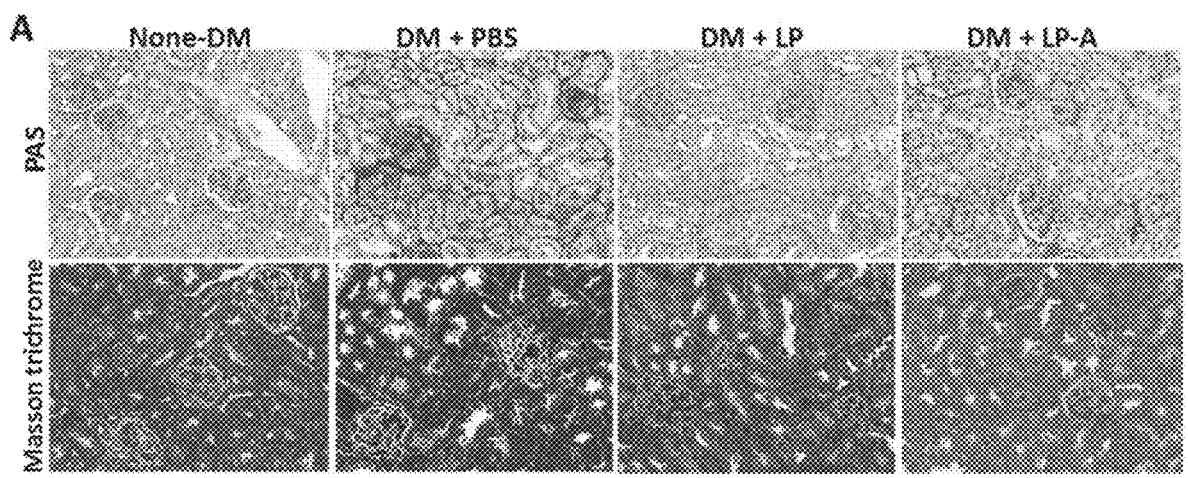
FIGS. 11A-11B show the effect of LP-A on renal damage in diabetic mice.
Figure 11B:
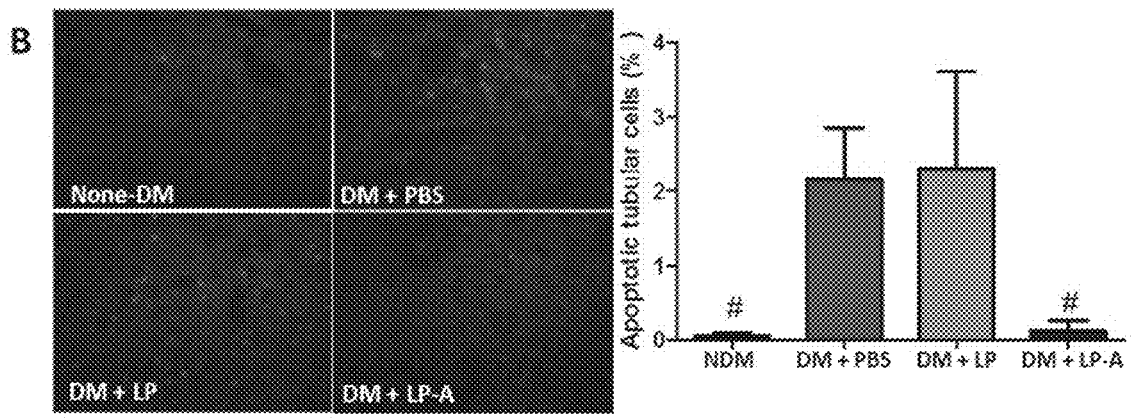
Figure 11C:
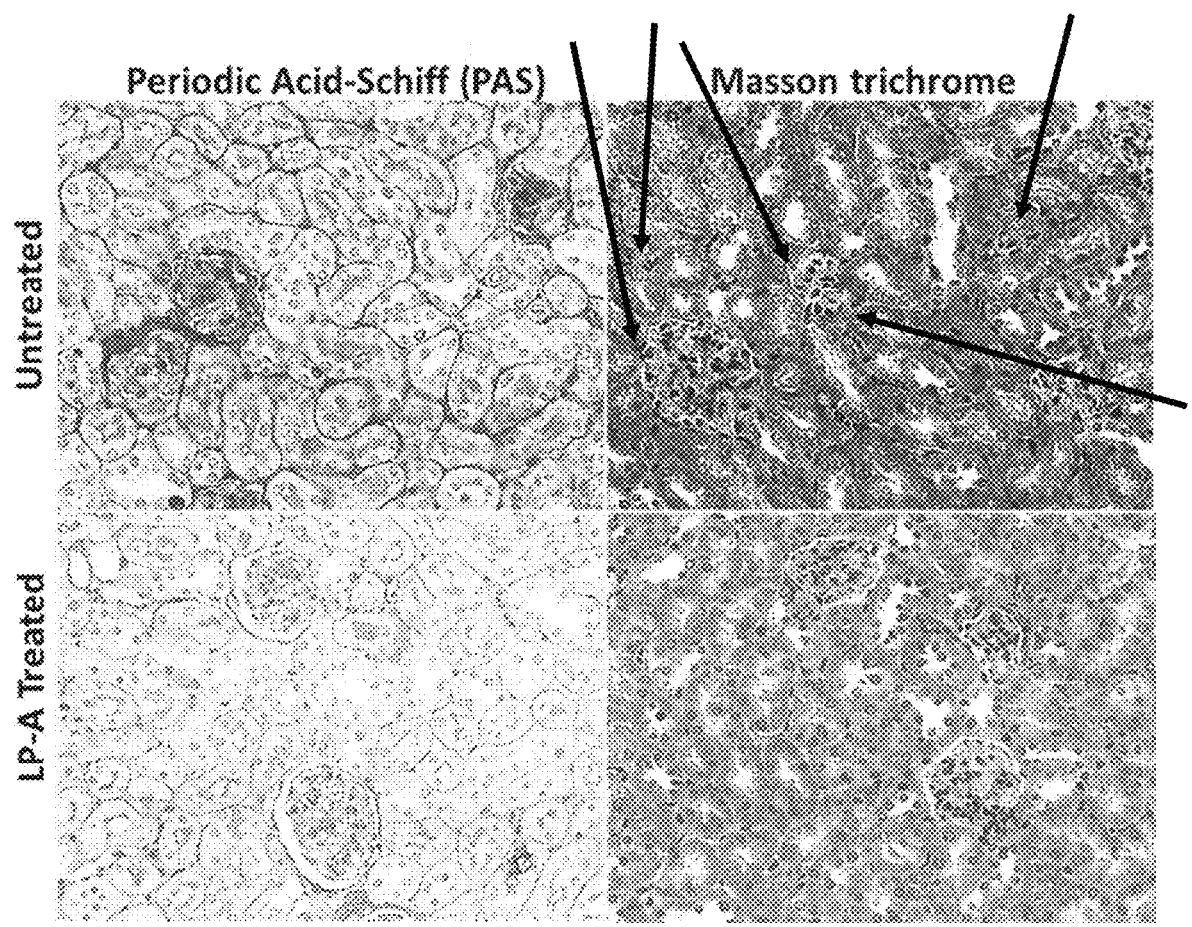
FIG. 11C shows that Oral administration of *Lactobacillus paracasei*-Ang-(1-7) (LP-A) prevents diabetes-induced nephropathy in diabetic eNOS−/− mice. Diabetic mice show renal hypertrophy, nodular lesion with acellular periodic acid-Schiff (PAS)-positive staining material, diffuse glomerulosclerosis, and fibrosis as shown as intense staining (shown by arrows) in Masson trichrome staining, these pathologic changes are prevented in mice treated with *Lactobacillus paracasei*-Ang-(1-7) (LP-A). N=4.
Figures 12A, 12B, 12C, 12D:
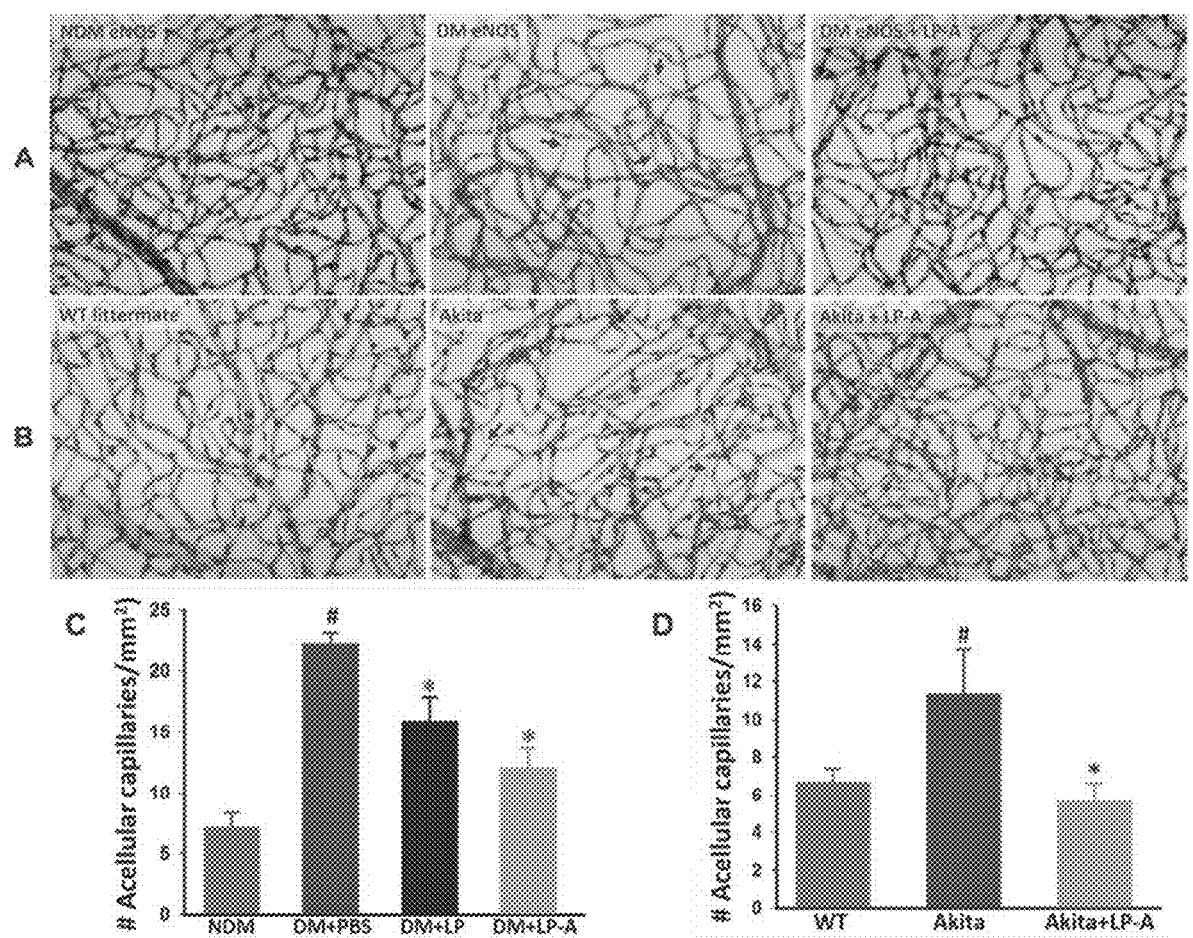
FIGS. 12A-12D show an evaluation of retinal acellular capillary in untreated and LP, LP-A treated retinas of diabetic mice.
Figure 12E:
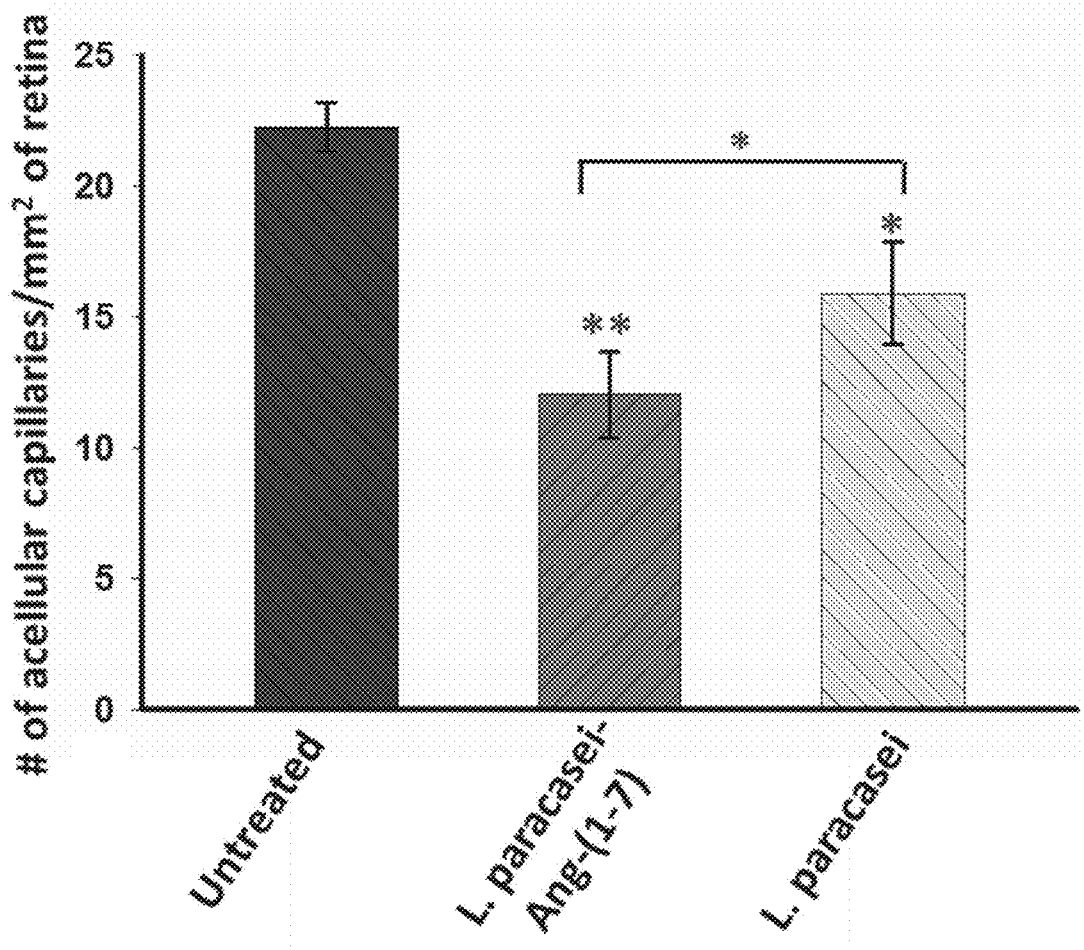
FIG. 12E shows that oral administration of *Lactobacillus paracasei*-Ang-(1-7) (LP-A) prevents diabetes-induced retinopathy in diabetic eNOS−/− mice. Diabetic mice show increased retinal vascular capillary loss, this is prevented in mice treated with LP-A. N=6/group. Error bars represent standard deviation. **p<0.01 (vs untreated control). *p<0.05 (vs untreated control and *L. paracasei* alone).

To test whether oral delivery of probiotic-expressed Ang-(1-7) confer protection against diabetes and its complications, diabetic eNOS mice, which develop accelerated diabetic nephropathy [43] and retinopathy [44], were used. Diabetes was induced by intraperitoneal injection of streptozotocin (STZ). Oral administration of LP-A, LP, or saline (1010 cfu/mouse, twice/week) was started one week after STZ injection and was continued for 8 weeks. Results showed that oral feeding of LP and LP-A significantly improved STZ-induced damage to insulin producing beta cells in pancreas, improved structure and morphology of islets and increased insulin expression in diabetic eNOS-/- mice (FIG. 10F). Oral administration of LP-A also showed protective effects against diabetes-induced nephropathy (FIG. 11) and retinopathy (FIG. 12E).

Summary of Results

These results demonstrate that oral administration of a genetically modified bacterium that can secrete Ang-(1-7) provides protection against diabetes and diabetic complications.

Oral Delivery of Probiotics Expressing Ang-(1-7) Improves Glucose Tolerance and Insulin Sensitivity The fasted-state blood glucose levels were lower in diabetic mice treated with LP-A (FIG. 10B). Glucose tolerance tests (GTTs) showed that oral of LP-GFP or LP-A could improve the glucose tolerance in diabetic mice (FIG. 10C, D). However statistically significant difference was observed only in LP-A treated group when compared with PBS-treated control group. To evaluate insulin sensitivity of peripheral tissues, insulin tolerance tests (ITTs) were performed in mice. Diabetic mice with PBS treatment showed the lower blood glucose at 90 and 120 min points (FIG. 10E) which could be a result of lower insulin clearance due to kidney injury in diabetic mice.

Oral Administration of Lactobacillus paracasei-Ang-(1-7) Prevents Diabetes-Induced Destruction of Insulin Producing Cells and Increases Insulin Levels in Diabetic Mice.

Figure 10G:
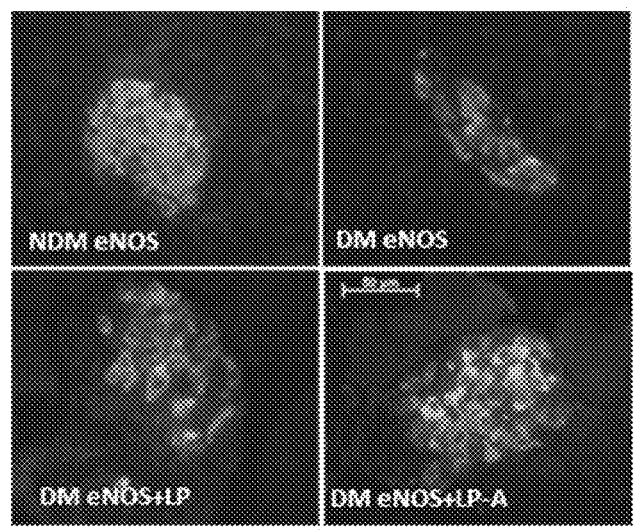
FIGS. 10G-10I show LP-A treatment increased insulin levels in islet (FIG. 10G), detected by immunofluorescence (insulin: green), and plasma detected by ELISA in diabetic eNOS (FIG. 10H) and Akita mice (FIG. 10I). Values are mean±SD; #: vs NDM/WT, P<0.001; *: vs DM, P<0.005. n=6-8/group.
Figure 10H:
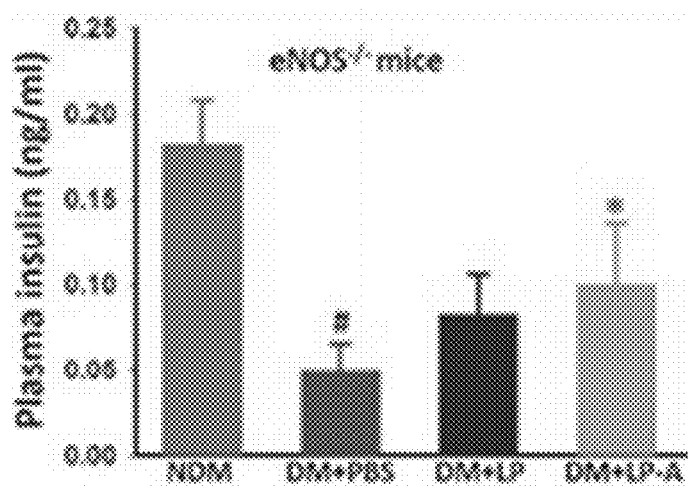
Figure 10I:
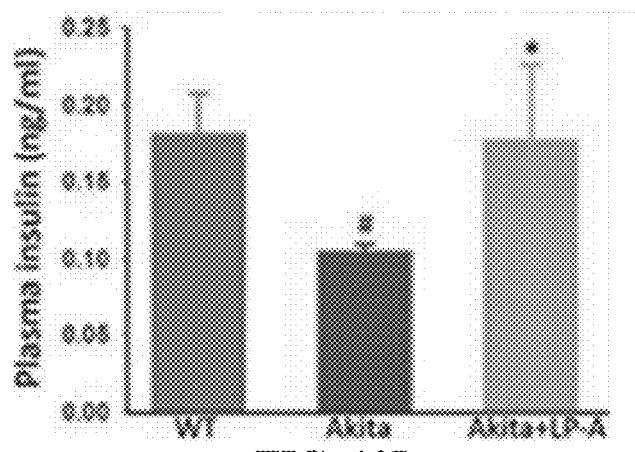

The morphology and insulin expression of the pancreatic islets, and plasma insulin level in mice was examined. Our results show that oral feeding of LP and LP-A significantly improved STZ-induced damage to insulin producing beta cells in pancreas, improved structure and morphology of islets and increased insulin expression in diabetic eNOS-/- mice (FIG. 10F), and observed higher insulin levels in islet R cells and plasma in LP-A treated mice than PBS diabetic (DM) group in both diabetic eNOS and the Akita mice (FIGS. 10G-I). No obvious apoptosis and proliferation were found in pancreatic islets in any diabetic mice groups (data not shown).

Oral Delivery of LP-A Alleviates the Damage in Kidney of Diabetic Mice

Histological assessment with Periodic Acid Schiff (PAS) staining for polysaccharides showed tubular damage after diabetes in mice. Additional Masson's Trichrome staining for fibrosis development (collagen appears blue) showed glomerular basement membrane thickening and renal interstitial fibrosis in diabetic mice. Positive staining for deposits of glycogen (in red) and collagen (in blue) were readily observed in the glomerular tuft and in the tubular epithelia of kidneys from DM+PBS and DM+LP groups, while being minimally increased in diabetic mice treated with LP-A (FIG. 11A). TUNEL assay was used to evaluate the cell death in kidneys from DM mice and in mice fed with LP-A. FIG. 11B showed a significant (P<001) decrease in TUNEL-positive cells in the kidney from diabetic mice fed with LP-A compared to DM group.

Oral Administration of LP-A Prevent Diabetes-Induced Retinal Capillary Loss in Mice Diabetes resulted in severe capillary loss in eNOS$^{-/-}$ (FIGS. 12A and C) as reported previously[20]. Akita mice show fewer retinal acellular capillaries (FIGS. 12B and D). LP-A treatment significantly reduced acellular capillaries in diabetic eNOS mice and completely prevented capillary loss in Akita mice (FIGS. 12B and D). LP alone also significantly reduced diabetes-induced retinal capillary loss compared to untreated animals (FIGS. 12A and C).

Figure 12F:
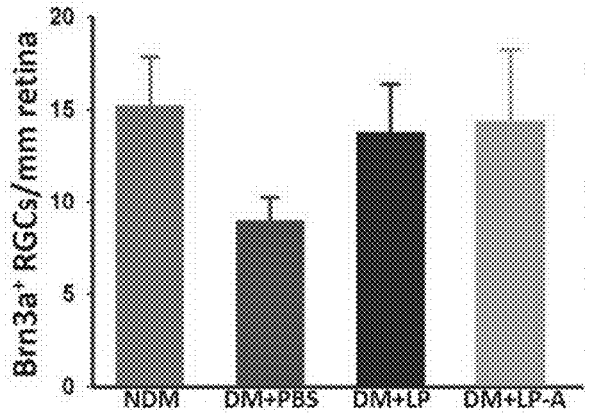
FIGS. 12F-12G show quantification of RGCs detected by Brn3a immunostaining (FIG. 12F) and activated microglial cells detected by Iba-1 immunofluorescence (FIG. 12G). NDM, nondiabetic; DM, diabetic. # (p<0.01): versus non-diabetic control; *(p<0.01): versus untreated DM groups).
Figure 12G:
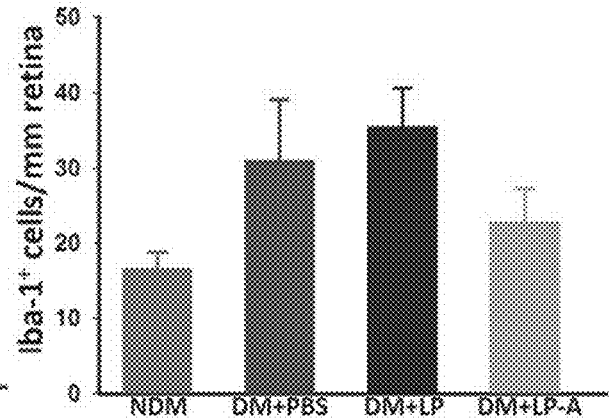

Oral Administration of L. paracasei-Ang-(1-7) Reduce Diabetes-Induced Retinal Ganglion Cell Loss, Gliosis and Expression of Inflammatory Cytokines in Diabetic Retina in Mice Diabetes resulted in increased RGCs loss, detected by Brn3a immunostaining (FIG. 12F) and microglial activation, detected by Iba-1 immunostaining (FIG. 12G). LP-A treatment prevented RGCs loss and microglial activation. Interestingly, LP alone also significantly prevented RGC loss, but had no effect on microglial activation.

Figure 12H:
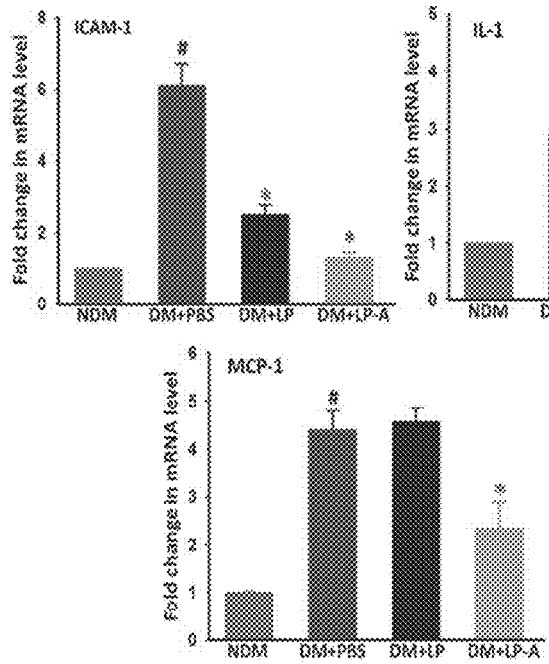
FIG. 12H shows graphs of real-time RT-PCR analysis of retinal mRNA levels of inflammatory cytokines including ICAM-1, IL-1, IL-6, MCP-1, and TNFalpha. Values on y-axis represent fold difference compared to age-matched nondiabetic retinal samples for each gene. NDM, nondiabetic; DM, diabetic. # (p<0.01): versus non-diabetic control; *(p<0.01): versus untreated DM groups).
Figure 12H:
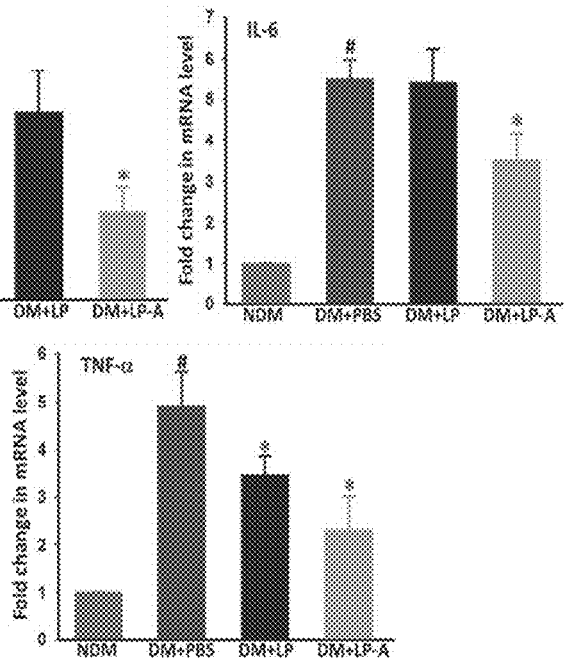

Real-time RT-PCR was used to evaluate the expression level of pro-inflammatory cytokines and chemokines in the retina from each experimental group. Diabetes induced increased retinal expression of ICAM-1, MCP1, IL-1 and TNF-α (FIG. 12H). LP-A treated animals show significantly decreased retinal expression of all these cytokines and chemokines, LP alone also reduced the expression of ICAM-1 and TNF-α, but had no effect on the expression of MCP1 and IL-1.

Example 4: Efficacy of Orally Administered Probiotic Bacteria Genetically Engineered to Express and Secrete Ang-(1-7) in Ocular Inflammation Oral Administration of Lactobacillus paracasei-Ang-(1-7) Prevents Experimental Autoimmune Uveitis (EAU) in Mice.

Figure 13:
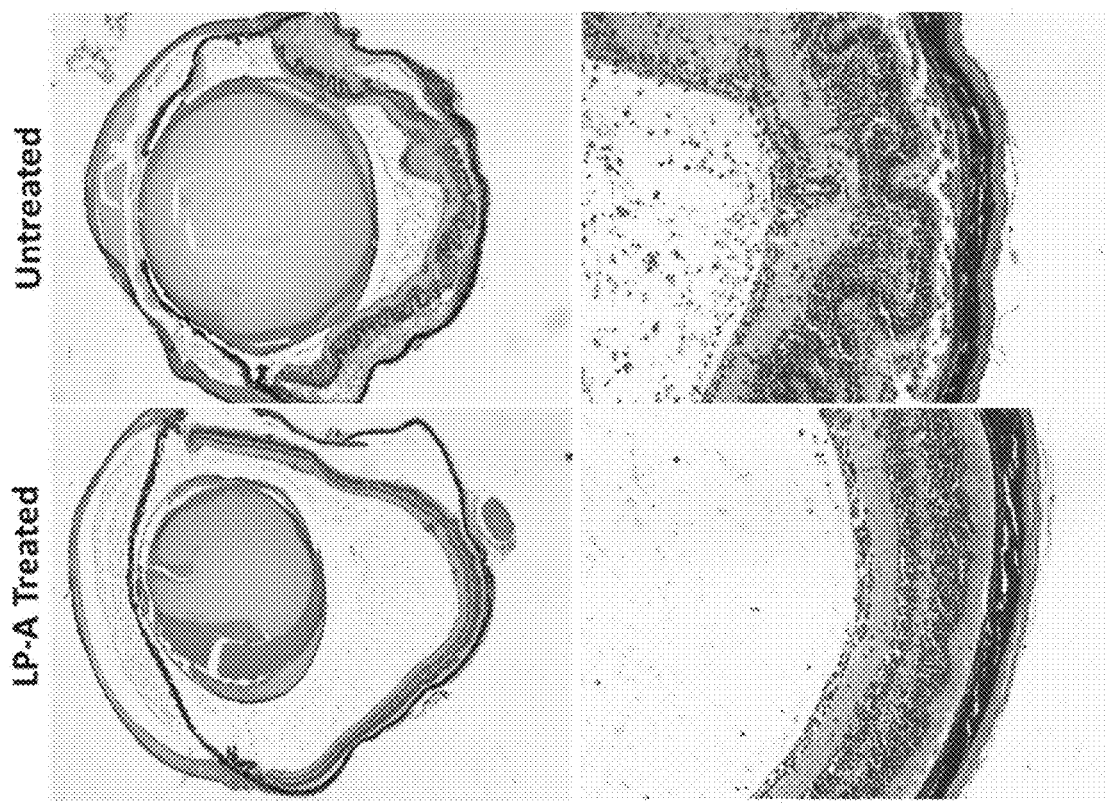
FIG. 13 shows histological evaluation of autoimmune uveitis (EAU) from hematoxylin and eosin-stained paraffin sections from untreated and LP-A treated mice. Left panel: lower magnification (original 2.5×). Right panel: higher magnification (original 20×). EAU eyes show severe intraocular inflammation evidenced by massive infiltration of inflammatory cells, intensive retinal vasculitits, and excessive folding and photoreceptor damage in untreated mice. Oral administration of LP-A dramatically reduced the inflammatory responses and retinal damage.
Figure 14:
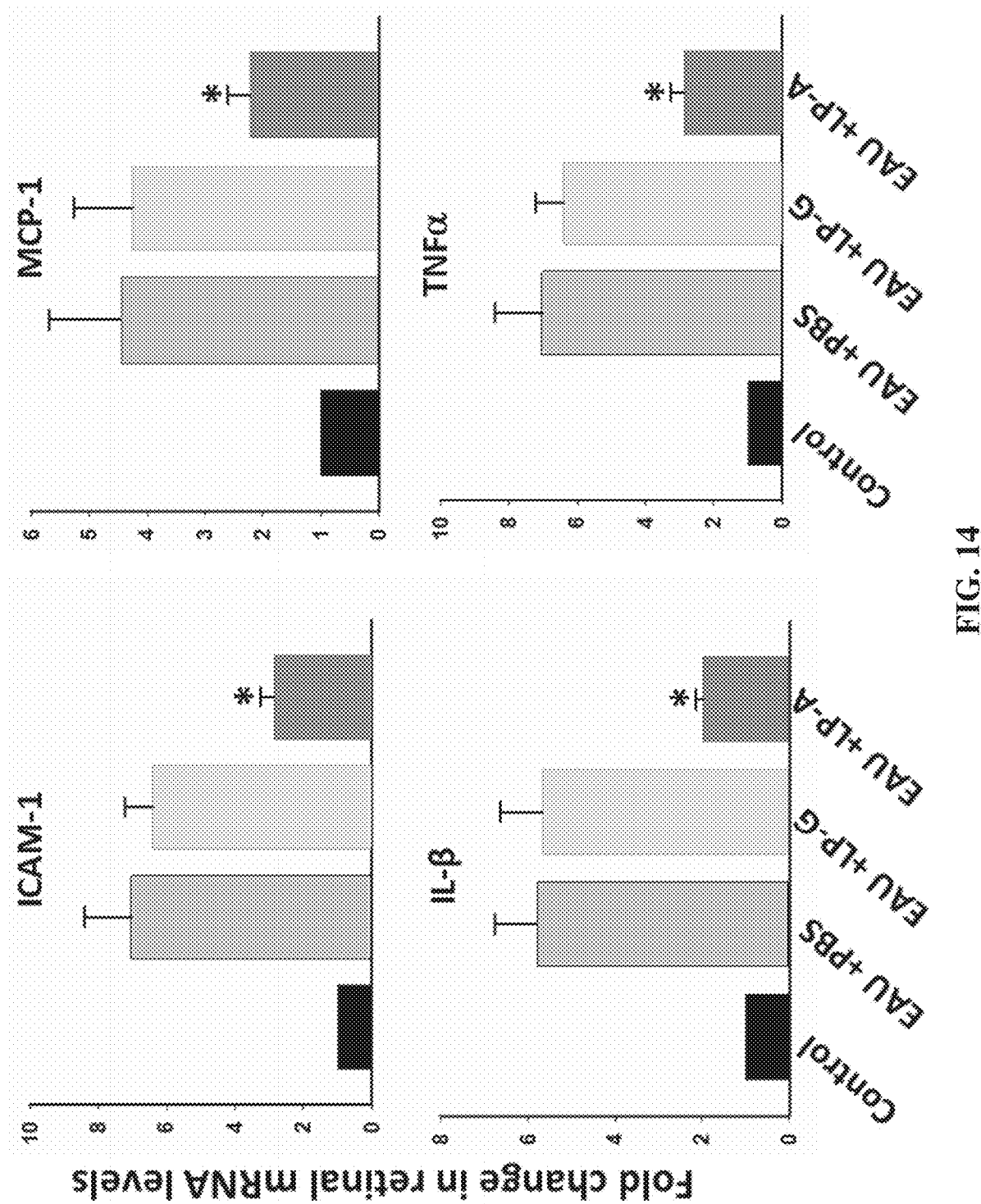
FIG. 14 shows that oral administration of LP-A reduced inflammatory cytokine expression in the EAU retina. Whole eyecups were used for analyzing the mRNA levels of the inflammatory cytokines: ICAM-1, MCP-1, TNF-a, and IL-1β by Real-time RT-PCR. Values on the y-axis represent the fold changes. All values were normalized to the untreated control. *P<0.001 (versus saline treated EAU group).

The anti-inflammatory effect of Ang-(1-7) has been well-established. To test whether probiotic-expressed Ang-(1-7) confer protection against ocular inflammation, the mouse experimental autoimmune uveitis (EAU) model was used. EAU was induced by active immunization with ~50 µg of interphotoreceptor retinoid-binding protein (IRBP, 161-180, SGIPYIISYLHPGNTILHVD, SEQ ID NO: 17), which was obtained from Genscript (Piscataway, N.J.) and emulsified in complete Freund's adjuvant (CFA) (1:1 vol/vol) subcutaneously, followed by daily administration of $10^{10}$ cfu/mouse of Lactobacillus paracasei expressing Ang (1-7) or saline for 14 days. The EAU mice were euthanized and the eyes were harvested on 14th day after immunization, and then evaluated by histopathology and molecular analysis. Oral administration of Lactobacillus paracasei-Ang-(1-7) dramatically reduced the inflammatory responses and retinal damage (FIG. 13), and significantly reduced retinal expression of pro-inflammatory cytokines (FIG. 14).

Summary of Results

These results demonstrate that oral administration of a genetically modified bacterium that can secrete Ang-(1-7) provides protection against inflammatory conditions of the eye.

Example 5: Efficacy of Orally Administered Probiotic Bacteria Genetically Engineered to Express and Secrete ACE2 in PH, Ocular Inflammation, and Diabetes An expression vector is made that can be used to genetically modify Lactobacillus paracasei so that the genetically modified bacteria express ACE2 fused to a carrier protein. In one version, the carrier protein is CTB and encoded by SEQ ID NO: 3. In another version of the ACE2 expression vector, the carrier protein is a CPP derived from PDX-1 and is encoded by SEQ ID NO: 18. In a third and fourth version of the ACE2 expression vector, ACE2 is fused to a carrier protein without a cleavage site.

Characterization of in vivo expression of ACE2 in mice orally fed with lactobacillus modified to comprise the expression vectors described above can be done in a manner described in Example 1. It is expected that ACE2 reaches target tissues similar to Ang-(1-7) delivered in a similar manner.

It was found in initial experiments that CTB-ACE2 fusion does not affect ACE2 activity.

Efficacy of orally administered probiotic bacteria genetically engineered to express and secrete ACE2 in pulmonary hypertension, diabetes and diabetic complications, and ocular inflammation can be tested according to methods described in Examples 2, 3 and 4. It is expected that orally administered probiotic bacteria genetically engineered to express and secrete ACE2 reduce symptoms of pulmonary hypertension, diabetes and diabetic complications, and ocular inflammation. It is also expected that the therapeutic benefit of delivering both Ang-(1-7) and ACE be at least as good, if not better, compared to delivery of Ang-(1-7) or ACE2 alone.

Figure 15:
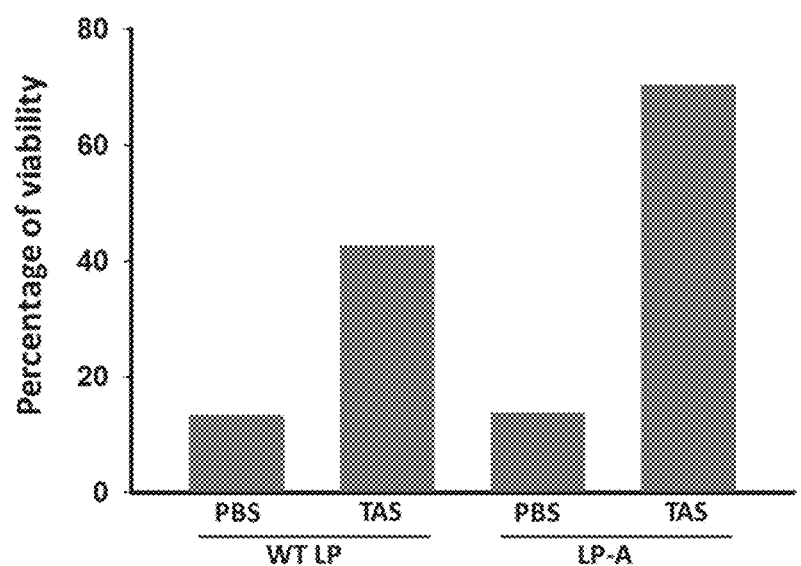
FIG. 15 shows viability of wild-type (WT) *Lactobacillus paracasei* (LP) and LP expressing Ang-(1-7) (LP-A) in PBS or TAS media.

Example 7: Lyophilized Wild-Type (WT) *Lactobacillus paracasei* (LP) or LP Expressing Ang-(1-7) Bacteria are Viable and Show Extend Colonization in Mice LP or LP-A bacteria lyophilized in PBS are viable (~13% compared to freshly prepared bacteria), and the viability is significantly improved when bacteria are lyophilized in medium containing 4% Trehalose+4% Ascorbate+6% skim milk (TAS), −42% for LP and 70% for LP-A (FIG. 15). Lyophilization allows much extended storage and shelf life.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

REFERENCES

1. Santos R A, Campagnole-Santos M J, Andrade S P: Angiotensin-(1-7): an update. *Regulatory peptides* 2000, 91(1-3):45-62.
2. Campagnole-Santos M J, Diz D I, Santos R A, Khosla M C, Brosnihan K B, Ferrario C M: Cardiovascular effects of angiotensin-(1-7) injected into the dorsal medulla of rats. *The American journal of physiology* 1989, 257(1 Pt 2):H324-329.
3. Schiavone M T, Santos R A, Brosnihan K B, Khosla M C, Ferrario C M: Release of vasopressin from the rat hypothalamo-neurohypophysial system by angiotensin-(1-7) heptapeptide. *Proceedings of the National Academy of Sciences of the United States of America* 1988, 85(11):4095-4098.
4. Santos R A, Simoes e Silva A C, Marie C, Silva D M, Machado R P, de Buhr I, Heringer-Walther S, Pinheiro S V, Lopes M T, Bader M et al: Angiotensin-(1-7) is an endogenous ligand for the G protein-coupled receptor Mas. *Proceedings of the National Academy of Sciences of the United States of America* 2003, 100(14):8258-8263.
5. Simoes E S A, Silveira K, Ferreira A, Teixeira M: ACE2, angiotensin-(1-7) and Mas receptor axis in inflammation and fibrosis. *British journal of pharmacology* 2013, 169(3):477-492.
6. Passos-Silva D G, Verano-Braga T, Santos R A: Angiotensin-(1-7): beyond the cardio-renal actions. *Clinical science* 2013, 124(7):443-456.
7. Santos R A: Angiotensin-(1-7). *Hypertension* 2014, 63(6):1138-1147.
8. Santos S H, Andrade J M: Angiotensin 1-7: a peptide for preventing and treating metabolic syndrome. *Peptides* 2014, 59:34-41.
9. Dominici F P, Burghi V, Munoz M C, Giani J F: Modulation of the action of insulin by angiotensin-(1-7). *Clinical science* 2014, 126(9):613-630.
10. Qi Y, Zhang J, Cole-Jeffrey C T, Shenoy V, Espejo A, Hanna M, Song C, Pepine C J, Katovich M J, Raizada M K: Diminazene aceturate enhances Angiotensin-converting enzyme 2 activity and attenuates ischemia-induced cardiac pathophysiology. *Hypertension* 2013, 62(4):746-752.
11. Shenoy V, Ferreira A J, Qi Y, Fraga-Silva R A, Diez-Freire C, Dooies A, Jun J Y, Sriramula S, Mariappan N, Pourang D et al: The angiotensin-converting enzyme 2/angiogenesis-(1-7)/Mas axis confers cardiopulmonary protection against lung fibrosis and pulmonary hypertension. *Am J Respir Crit Care Med* 2010, 182(8):1065-1072.
12. Shenoy V, Gjymishka A, Jarajapu Y P, Qi Y, Afzal A, Rigatto K, Ferreira A J, Fraga-Silva R A, Kearns P, Douglas J Y et al: Diminazene attenuates pulmonary hypertension and improves angiogenic progenitor cell functions in experimental models. *Am J Respir Crit Care Med* 2013, 187(6):648-657.
13. Shenoy V, Kwon K C, Rathinasabapathy A, Lin S, Jin G, Song C, Shil P, Nair A, Qi Y, Li Q et al: Oral delivery of Angiotensin-converting enzyme 2 and Angiotensin-(1-7) bioencapsulated in plant cells attenuates pulmonary hypertension. *Hypertension* 2014, 64(6):1248-1259.
14. Qiu Y, Shil P K, Zhu P, Yang H, Verma A, Lei B, Li Q: Angiotensin-converting enzyme 2 (ACE2) activator diminazene aceturate ameliorates endotoxin-induced uveitis in mice. *Investigative ophthalmology & visual science* 2014, 55(6):3809-3818.
15. Shil P K, Kwon K C, Zhu P, Verma A, Daniell H, Li Q: Oral delivery of ACE2/Ang-(1-7) bioencapsulated in plant cells protects against experimental uveitis and autoimmune uveoretinitis. *Molecular therapy: the journal of the American Society of Gene Therapy* 2014, 22(12):2069-2082.
16. Verma A, Shan Z, Lei B, Yuan L, Liu X, Nakagawa T, Grant M B, Lewin A S, Hauswirth W W, Raizada M K et al: ACE2 and Ang-(1-7) confer protection against development of diabetic retinopathy. *Molecular therapy: the journal of the American Society of Gene Therapy* 2012, 20(1):28-36.
17. Loot A E, Roks A J, Henning R H, Tio R A, Suurmeijer A J, Boomsma F, van Gilst W H: Angiotensin-(1-7) attenuates the development of heart failure after myocardial infarction in rats. *Circulation* 2002, 105(13):1548-1550.
18. Pereira R M, Dos Santos R A, Teixeira M M, Leite V H, Costa L P, da Costa Dias F L, Barcelos L S, Collares G B, Simoes e Silva A C: The renin-angiotensin system in a rat model of hepatic fibrosis: evidence for a protective role of Angiotensin-(1-7). *J Hepatol* 2007, 46(4):674-681.
19. Santos R A, Frezard F, Ferreira A J: Angiotensin-(1-7): blood, heart, and blood vessels. *Curr Med Chem Cardiovasc Hematol Agents* 2005, 3(4):383-391.
20. Santos R A, Ferreira A J, Nadu A P, Braga A N, de Almeida A P, Campagnole-Santos M J, Baltatu O, Iliescu R, Reudelhuber T L, Bader M: Expression of an angiotensin-(1-7)-producing fusion protein produces cardioprotective effects in rats. *Physiological genomics* 2004, 17(3):292-299.
21. Menon J, Soto-Pantoja D R, Callahan M F, Cline J M, Ferrario C M, Tallant E A, Gallagher P E: Angiotensin-(1-7) inhibits growth of human lung adenocarcinoma xenografts in nude mice through a reduction in cyclooxygenase-2. *Cancer Res* 2007, 67(6):2809-2815.

22. Heringer-Walther S, Eckert K, Schumacher S M, Uharek L, Wulf-Goldenberg A, Gembardt F, Fichtner I, Schultheiss H P, Rodgers K, Walther T: Angiotensin-(1-7) stimulates hematopoietic progenitor cells in vitro and in vivo. *Haematologica* 2009, 94(6):857-860.

23. Jarajapu Y P, Bhatwadekar A D, Caballero S, Hazra S, Shenoy V, Medina R, Kent D, Stitt A W, Thut C, Finney E M et al: Activation of the ACE2/Angiotensin-(1-7)/Mas Receptor xis Enhances the Reparative Function of Dysfunctional Diabetic Endothelial Progenitors. *Diabetes* 2013, 62(4):1258-1269.

24. Langeveld B, van Gilst W H, Tio R A, Zijlstra F, Roks A J: Angiotensin-(1-7) attenuates neointimal formation after stent implantation in the rat. *Hypertension* 2005, 45(1):138-141.

25. Iusuf D, Henning R H, van Gilst W H, Roks A J: Angiotensin-(1-7): pharmacological properties and pharmacotherapeutic perspectives. *European journal of pharmacology* 2008, 585(2-3):303-312.

26. Trask A J, Ferrario C M: Angiotensin-(1-7): pharmacology and new perspectives in cardiovascular treatments. *Cardiovasc Drug Rev* 2007, 25(2):162-174.

27. Simoes e Silva A C, Pinheiro S V, Pereira R M, Ferreira A J, Santos R A: The therapeutic potential of Angiotensin-(1-7) as a novel Renin-Angiotensin System mediator. *Mini Rev Med Chem* 2006, 6(5):603-609.

28. Rodgers K E, Oliver J, diZerega G S: Phase I/II dose escalation study of angiotensin 1-7 [A(1-7)] administered before and after chemotherapy in patients with newly diagnosed breast cancer. *Cancer Chemother Pharmacol* 2006, 57(5):559-568.

29. Petty W J, Miller A A, McCoy T P, Gallagher P E, Tallant E A, Torti F M: Phase I and pharmacokinetic study of angiotensin-(1-7), an endogenous antiangiogenic hormone. *Clin Cancer Res* 2009, 15(23):7398-7404.

30. Yamada K, Iyer S N, Chappell M C, Ganten D, Ferrario C M: Converting enzyme determines plasma clearance of angiotensin-(1-7). *Hypertension* 1998, 32(3):496-502.

31. Allred A J, Diz D I, Ferrario C M, Chappell M C: Pathways for angiotensin-(1-7) metabolism in pulmonary and renal tissues. *American journal of physiology Renal physiology* 2000, 279(5):F841-850.

32. Nussenblatt R B, Gery I, Weiner H L, Ferris F L, Shiloach J, Remaley N, Perry C, Caspi R R, Hafler D A, Foster C S et al: Treatment of uveitis by oral administration of retinal antigens: results of a phase I/II randomized masked trial. *American journal of ophthalmology* 1997, 123(5):583-592.

33. Thurau S R, Diedrichs-Mohring M, Fricke H, Burchardi C, Wildner G: Oral tolerance with an HLA-peptide mimicking retinal autoantigen as a treatment of autoimmune uveitis. *Immunology letters* 1999, 68(2-3):205-212.

34. Commins S P: Mechanisms of Oral Tolerance. *Pediatr Clin North Am* 2015, 62(6):1523-1529.

35. Mizock B A: Probiotics. *Disease-a-month: DM* 2015, 61(7):259-290.

36. Vitetta L, Briskey D, Alford H, Hall S, Coulson S: Probiotics, prebiotics and the gastrointestinal tract in health and disease. *Inflammopharmacology* 2014, 22(3):135-154.

37. Butel M J: Probiotics, gut microbiota and health. *Med Mal Infect* 2014, 44(1):1-8.

38. Lizier M, Sarra P G, Cauda R, Lucchini F: Comparison of expression vectors in *Lactobacillus reuteri* strains. *FEMS microbiology letters* 2010, 308(1):8-15.

39. Kajikawa A, Ichikawa E, Igimi S: Development of a highly efficient protein-secreting system in recombinant *Lactobacillus casei*. Journal of microbiology and biotechnology 2010, 20(2):375-382.

40. Rodighiero C, Fujinaga Y, Hirst T R, Lencer W I: A cholera toxin B-subunit variant that binds ganglioside G(M1) but fails to induce toxicity. The Journal of biological chemistry 2001, 276(40):36939-36945.

41. Aman A T, Fraser S, Merritt E A, Rodigherio C, Kenny M, Ahn M, Hol W G, Williams N A, Lencer W I, Hirst T R: A mutant cholera toxin B subunit that binds GM1-ganglioside but lacks immunomodulatory or toxic activity. Proceedings of the National Academy of Sciences of the United States of America 2001, 98(15): 8536-8541.

42. Padda R S, Shi Y, Lo C S, Zhang S L, Chan J S: Angiotensin-(1-7): A Novel Peptide to Treat Hypertension and Nephropathy in Diabetes? J Diabetes Metab 2015, 6(10).

43. Nakagawa T, Sato W, Glushakova O, Heinig M, Clarke T, Campbell-Thompson M, Yuzawa Y, Atkinson M A, Johnson R J, Croker B: Diabetic endothelial nitric oxide synthase knockout mice develop advanced diabetic nephropathy. Journal of the American Society of Nephrology: JASN 2007, 18(2):539-550.

44. Li Q, Verma A, Han P Y, Nakagawa T, Johnson R J, Grant M B, Campbell-Thompson M, Jarajapu Y P, Lei B, Hauswirth W W: Diabetic eNOS-knockout mice develop accelerated retinopathy. Investigative ophthalmology & visual science 2010, 51(10):5240-5246.

What is claimed is:

1. An expression vector comprising a polynucleic acid for expressing ACE2 in a bacterium, the polynucleic acid comprising:
   a promoter,
   a nucleic acid encoding a secretion signal peptide,
- a nucleic acid encoding a carrier protein, wherein the nucleic acid encoding the carrier protein has:
  - (i) a polynucleic acid sequence having at least 80% sequence identity to SEQ ID NO: 3 or
  - (ii) a polynucleic acid sequence having at least 95% sequence identity to SEQ ID NO: 18,
- a nucleic acid encoding ACE2, and;
- wherein the nucleic acids encoding the secretion signal peptide, carrier protein and ACE2 encode a fusion protein and are operably linked to the promoter.

2. The expression vector of claim 1, further comprising a nucleic acid encoding a cleavage site that lies in between the nucleic acids encoding the carrier protein and ACE2.

3. The expression vector of claim 1, further comprising a nucleic acid encoding a hinge that lies 3' to the nucleic acid encoding the carrier protein.

4. The expression vector of claim 1, wherein the promoter is a lactose dehydrogenase (ldh) promoter from *Lactococcus lactis*.

5. The expression vector of claim 4, wherein sequence of the ldh promoter is at least 95% identical to SEQ ID NO: 1.

6. The expression vector of claim 5, wherein sequence of the ldh promoter is SEQ ID NO: 1.

7. The expression vector of claim 1, wherein the secretion signal peptide is from the usp45 gene of *Lactococcus lactis*.

8. The expression vector of claim 7, wherein sequence of the nucleic acid encoding the secretion signal peptide from usp45 gene of *Lactococcus lactis* is at least 95% identical to SEQ ID NO: 2.

9. The expression vector of claim 8, wherein sequence of the nucleic acid encoding the secretion signal peptide from usp45 gene of *Lactococcus lacti* is SEQ ID NO: 2.

10. The expression vector of claim 1, wherein the nucleic acid encoding the secretion signal peptide lies adjacent and 5' to the nucleic acid encoding the carrier protein.

11. The expression vector of claim 1, wherein the carrier protein is cholera toxin B (CTB), and wherein the sequence of the nucleic acid encoding CTB is at least 95% identical to SEQ ID NO: 3.

12. The expression vector of claim 1, wherein the sequence of the nucleic acid encoding CTB is SEQ ID NO: 3.

13. The expression vector of claim 1, wherein the carrier protein is a cell-penetrating peptide (CPP) derived from Pancreatic And Duodenal Homeobox I (PDX-1), and wherein the nucleic acid encoding the CPP is as set forth in SEQ ID NO: 18.

14. The expression vector of claim 1, wherein the sequence of the nucleic acid encoding ACE2 is at least 95% identical to SEQ ID NO: 7.

15. The expression vector of claim 1, wherein the sequence of the nucleic acid encoding ACE2 is SEQ ID NO: 7.

16. The expression vector of claim 2, wherein the cleavage site is a furin cleavage site.

17. A genetically engineered bacterium comprising the expression vector of claim 1.

18. The genetically engineered bacterium of claim 17, wherein the bacterium is a *Lactobacillus*.

19. The genetically engineered bacterium of claim 18, wherein the *Lactobacillus* is *L. paracasei, L. plantarum* or *L. gasseri*.

20. A probiotic composition comprising a plurality of the genetically engineered bacterium of claim 17, wherein the bacteria are concentrated and live, frozen, in lyophilized powder form or lyophilized tablet form.

21. A method of treating a disease or condition involving the renin-angiotensin system (RAS), the method comprising administering orally to a subject in need thereof a therapeutically effective dose of the probiotic composition of claim 20.

* * * * *

SEQUENCE LISTING

<160> NUMBER OF SEQ ID NOS: 20

<210> SEQ ID NO 1
<211> LENGTH: 298
<212> TYPE: DNA
<213> ORGANISM: Lactococcus lactis

<400> SEQUENCE: 1

```
caagtctcct tttttattag tgataatttt aacaagaaa attataccat gttgaagagc      60
attaataaaa ttattatttt gtgtttgtgc tattatagtt gagattatta ttaatgaggg    120
gtaaataaga tgaagataat tgcaggtttg ggtaatccgg gtcaaaaata tgataagacc    180
aaacataata ctggtttcat gacaatggat cactaccttg ataaaaagg tttgacttta     240
```

```
aataaagata aatttgaagg gcattggact aaaaagctta tcgataccgt cgaccgat      298
```

<210> SEQ ID NO 2
<211> LENGTH: 96
<212> TYPE: DNA
<213> ORGANISM: Lactococcus lactis

<400> SEQUENCE: 2

```
atgaaaaaaa agattatctc agctatttta atgtctacag tgatactttc tgctgcagcc      60
ccgttgtcag gtgtttacgc tgacacaaac tcagat                                96
```

<210> SEQ ID NO 3
<211> LENGTH: 372
<212> TYPE: DNA
<213> ORGANISM: Artificial Sequence
<220> FEATURE:
<223> OTHER INFORMATION: Synthetic Polynucleotide

<400> SEQUENCE: 3

```
atgattaagt taaagtttgg tgtttttttt actgttttat tatcatcagc ttacgctcac      60
ggtactccac aaaacattac tgatttatgt gctgaatacc acaacactca aattcacact     120
ttaaacgata agatttttttc atacactgaa tcattagctg gtaagcgtga atggctatt     180 attactttta agaacggtgc tacttttcaa gttgaagttc aggttcaca agctattgat      240 tcacaaaaga aggctattga acgtatgaag gatactttac gtattgctta cttaactgaa     300
gctaaggttg aaaagttatg tgtttggaac aacaagactc cacacgctat tgctgctatt     360
tcaatggcta ac                                                          372
```

<210> SEQ ID NO 4
<211> LENGTH: 21
<212> TYPE: DNA
<213> ORGANISM: Homo sapiens

<400> SEQUENCE: 4

```
gatcgtgttt acattcatcc t                                                21
```

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 5

```
Gly Pro Gly Pro Ser Arg Lys Lys Arg
1               5
```

<210> SEQ ID NO 6
<211> LENGTH: 384
<212> TYPE: DNA
<213> ORGANISM: Artificial Sequence
<220> FEATURE:
<223> OTHER INFORMATION: Synthetic Polynucleotide

<400> SEQUENCE: 6

```
gtaattctca tgtttgacag cttatcatcg ataagcttta atgcggtagt ttatcacagt      60
taaattgcta acgcagtcag gcaccgtgta tgaaatctaa caatgcgctc atcgtcatcc     120
tcggcaccgt caccctggat gctgtaggca taggcttggt tatgccggta ctgccgggcc     180
tcttgcggga tatcgtccat tccgacagca tcgccagtca ctatggcgtg ctgctagcgc     240
```

| | | |
|---|---|---|
| tatatgcgtt gatgcaattt ctatgcgcac ccgttctcgg agcactgtcc gaccgctttg | 300 |
| gccgccgccc agtcctgctc gcttcgctac ttggagccac tatcgactac gcgatcatgg | 360 |
| cgaccacacc cgtcctgtgg atcc | 384 |

<210> SEQ ID NO 7
<211> LENGTH: 2416
<212> TYPE: DNA
<213> ORGANISM: Homo sapiens

<400> SEQUENCE: 7

| | |
|---|---|
| atgtcatcat catcatggtt gttgttgtca ttggttgctg ttaccgctgc tcaatcaacc | 60 |
| atcgaagaac aagctaagac cttcttggat aagttcaacc atgaagctga agatttgttc | 120 |
| tatcaatcat cattggcttc atggaactat aacaccaaca tcaccgaaga aaacgttcaa | 180 |
| aacatgaaca acgctggcga taagtggtca gctttcttga aggaacaatc aaccttggct | 240 |
| caaatgtatc cattgcaaga aatccaaaac ttgaccgtta agttgcaatt gcaagctttg | 300 |
| caacaaaacg gctcatcagt tttgtcagaa gataagtcaa agcgtttgaa caccatcttg | 360 |
| aacaccatgt caaccatcta ttcaaccggc aaggtttgca acccagataa cccacaagaa | 420 |
| tgcttgttgt tggaaccagg cttgaacgaa atcatggcta actcattgga ttataacgaa | 480 |
| cgtttgtggg cttgggaatc atggcgttca gaagttggca agcaattgcg tccattgtat | 540 |
| gaagaatatg ttgttttgaa gaacgaaatg gctcgtgcta accattatga agattatggc | 600 |
| gattattggc gtggcgatta tgaagttaac ggcgttgatg ctatgattta cacgtggc | 660 |
| caattgatcg aagatgttga acataccttc gaagaaatca gccattgta tgaacatttg | 720 |
| catgcttatg ttcgtgctaa gttgatgaac gcttatccat catatatctc accaatcggc | 780 |
| tgcttgccag ctcatttgtt gggcgatatg tggggccgtt tctggaccaa cttgtattca | 840 |
| ttgaccgttc cattcggcca aaagccaaac atcgatgtta ccgatgctat ggttgatcaa | 900 |
| gcttgggatg ctcaacgtat cttcaaggaa gctgaaaagt tcttcgtttc agttggcttg | 960 |
| ccaaacatga cccaaggctt ctgggaaaac tcaatgttga ccgatccagg caacgttcaa | 1020 |
| aaggctgttt gccatccaac cgcttgggat ttgggcaagg cgatttccg tatcttgatg | 1080 |
| tgcaccaagg ttaccatgga tgatttcttg accgctcatc atgaaatggg ccatatccaa | 1140 |
| tatgatatgc cttatgctgc tcaaccattc ttgttgcgta acggcgctaa cgaaggcttc | 1200 |
| catgaagctg ttggcgaaat catgtcattg tcagctgcta ccccaaagca tttgaagtca | 1260 |
| atcggcttgt tgtcaccaga tttccaagaa gataacgaaa ccgaaatcaa cttcttgttg | 1320 |
| aagcaagctt tgaccatcgt tggcaccttg ccattcacct atatgttgga aaagtggcgt | 1380 |
| tggatggttt tcaagggcga aatcccaaag gatcaatgga tgaagaagtg gtgggaaatg | 1440 |
| aagcgtgaaa tcgttggcgt tgttgaacca gttccacatg atgaaaccta ttgcgatcca | 1500 |
| gcttcattgt tccatgtttc aaacgattat tcattcatcc gttattatac ccgtaccttg | 1560 |
| tatcaattcc aattccaaga agctttgtgc caagctgcta agcatgaagg cccattgcat | 1620 |
| aagtgcgata tctcaaactc aaccgaagct ggccaaaagt tgttcaacat gttgcgtttg | 1680 |
| ggcaagtcag aaccatggac cttggctttg aaaacgttg ttggcgctaa gaacatgaac | 1740 |
| gttcgtccat tgttgaacta tttcgaacca ttgttcacct ggttgaagga tcaaaacaag | 1800 |
| aactcattcg ttggctggtc aaccgattgg tcaccatatg ctgatcaatc aatcaaggtt | 1860 |
| cgtatctcat tgaagtcagc tttgggcgat aaggcttatg aatggaacga taacgaaatg | 1920 |

```
tatttgttcc gttcatcagt tgcttatgct atgcgtcaat atttcttgaa ggttaagaac    1980
caaatgatct tgttcggcga agaagatgtt cgtgttgcta acttgaagcc acgtatctca    2040
ttcaacttct tcgttaccgc tccaaagaac gtttcagata tcatcccacg taccgaagtt    2100
gaaaaggcta tccgtatgtc acgttcacgt atcaacgatg ctttccgttt gaacgataac    2160
tcattggaat tcttgggcat ccaaccaacc ttgggcccac caaaccaacc accagtttca    2220
atctggttga tcgttttcgg cgttgttatg ggcgttatcg ttgttggcat cgttatcttg    2280
atcttcaccg gcatccgtga tcgtaagaag aagaacaagg ctcgttcagg cgaaaaccca    2340
tatgcttcaa tcgatatctc aaagggcgaa aacaacccag gcttccaaaa caccgatgat    2400
gttcaaacct cattct                                                   2416
```

```
<210> SEQ ID NO 8
<211> LENGTH: 32
<212> TYPE: PRT
<213> ORGANISM: Lactococcus lactis

<400> SEQUENCE: 8
```

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr Asn Ser Asp
            20                  25                  30

```
<210> SEQ ID NO 9
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 9
```

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile His Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Thr Phe Gln Val Glu Val Pro Gly Ser Gln Ala Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120

```
<210> SEQ ID NO 10
<211> LENGTH: 7
<212> TYPE: PRT
<213> ORGANISM: Homo sapiens

<400> SEQUENCE: 10
```

Asp Arg Val Tyr Ile His Pro
1               5

```
<210> SEQ ID NO 11
```

```
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 11

Ser Arg Lys Lys Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 12

Thr Arg Ser Arg Lys Lys Arg
1               5

<210> SEQ ID NO 13
<211> LENGTH: 805
<212> TYPE: PRT
<213> ORGANISM: Homo sapiens

<400> SEQUENCE: 13

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255
```

-continued

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

```
Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
                740                 745                 750

Ile Val Val Gly Ile Val Ile Leu Ile Phe Thr Gly Ile Arg Asp Arg
            755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
                805
```

```
<210> SEQ ID NO 14
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 14

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile His Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120
```

```
<210> SEQ ID NO 15
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 15
ggtcctggtc ct                                                           12
```

```
<210> SEQ ID NO 16
<211> LENGTH: 15
<212> TYPE: DNA
<213> ORGANISM: Artificial Sequence
<220> FEATURE:
```

<223> OTHER INFORMATION: Synthetic Polynucleotide

<400> SEQUENCE: 16
tcacgtaaga agcgt                                                        15

<210> SEQ ID NO 17
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 17

Ser Gly Ile Pro Tyr Ile Ile Ser Tyr Leu His Pro Gly Asn Thr Ile
1               5                   10                  15

Leu His Val Asp
            20

<210> SEQ ID NO 18
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 18
cgtcatatca agatctggtt ccaaaaccgt cgtatgaagt ggaagaag                    48

<210> SEQ ID NO 19
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 19

Arg His Ile Lys Ile Trp Phe Gln Asn Arg Arg Met Lys Trp Lys Lys
1               5                   10                  15

<210> SEQ ID NO 20
<211> LENGTH: 9
<212> TYPE: PRT
<213> ORGANISM: Homo sapiens

<400> SEQUENCE: 20

Asp Arg Val Tyr Ile His Pro Phe His
1               5